(12) United States Patent
Ford et al.

(10) Patent No.: US 9,286,443 B2
(45) Date of Patent: Mar. 15, 2016

(54) SYSTEMS AND METHODS FOR DATA AGGREGATION AND PRIORITIZATION

(75) Inventors: John P. Ford, Unadilla, NY (US); Liying Huang, State College, PA (US)

(73) Assignee: Rapid Systems, LLC, Unadilla, NY (US)

( * ) Notice: Subject to any disclaimer, the term of this patent is extended or adjusted under 35 U.S.C. 154(b) by 1044 days.

(21) Appl. No.: 13/345,939

(22) Filed: Jan. 9, 2012

(65) Prior Publication Data

US 2012/0105471 A1    May 3, 2012

Related U.S. Application Data

(63) Continuation-in-part of application No. 12/156,723, filed on Jun. 4, 2008, now Pat. No. 8,489,544.

(60) Provisional application No. 60/933,038, filed on Jun. 4, 2007.

(51) Int. Cl.
| | |
|---|---|
| *G09G 5/00* | (2006.01) |
| *G06F 19/00* | (2011.01) |
| *G06F 17/30* | (2006.01) |
| *G06F 3/0482* | (2013.01) |
| *G06F 3/0481* | (2013.01) |

(52) U.S. Cl.
CPC .......... *G06F 19/3487* (2013.01); *G06F 3/0482* (2013.01); *G06F 3/04817* (2013.01); *G06F 17/30994* (2013.01)

(58) Field of Classification Search
None
See application file for complete search history.

(56) References Cited

U.S. PATENT DOCUMENTS

| | | | | |
|---|---|---|---|---|
| 5,537,618 | A  * | 7/1996 | Boulton et al. | 715/745 |
| 6,295,062 | B1 * | 9/2001 | Tada et al. | 715/835 |
| 7,187,452 | B2 | 3/2007 | Jupp et al. | |
| 7,319,972 | B2 | 1/2008 | von Gonten et al. | |
| 7,966,577 | B2 * | 6/2011 | Chaudhri | G06F 3/0482 345/473 |
| 8,161,552 | B1 * | 4/2012 | Sun | G06F 21/566 726/22 |
| 8,645,865 | B2 * | 2/2014 | Ananian | G06F 3/0482 715/708 |
| 8,707,211 | B2 * | 4/2014 | Yasui | G06F 3/0482 715/834 |
| 8,719,729 | B2 * | 5/2014 | Smith | G06F 3/0486 715/789 |
| 9,035,949 | B1 * | 5/2015 | Oberheu | G06F 1/00 345/440 |

(Continued)

OTHER PUBLICATIONS

Title: Circle View—A new approach for visualizing time-related multidimensional data sets, Author: Keim et al. pp. 4, date: May/Jun. 2004, Publisher: ACM Advanced Visual Interfaces http://kops.uni-konstanz.de/bitstream/handle/123456789/5484/AVI04_CircleView.pdf?sequence=1.*

(Continued)

*Primary Examiner* — Jwalant Amin

(57) ABSTRACT

Computer-enabled systems and methods aggregate data related to a particular subject or field and present the data in a simplified display. The data is divided into predetermined categories, which are graphically displayed in a predetermined arrangement. Systems and methods differentiate and visually display critical data abnormalities separately from non-critical data. The systems and methods enable an observer to identify the critical deviations or anomalies of data with respect to a predetermined base line by an intuitive visual display of all of the data from any sized data universe on a single screen. The data is indexed at multiple display levels such as a stack of one patient's data, a stack of all patient data for the universe of patients of a single practitioner, or a group of practitioners of any size. A portion of the display preferably may be selected and expanded to show only that portion in greater detail.

18 Claims, 17 Drawing Sheets

(56) References Cited

U.S. PATENT DOCUMENTS

| | | | |
|---|---|---|---|
| 2002/0016719 A1* | 2/2002 | Nemeth et al. | 705/2 |
| 2003/0065555 A1 | 4/2003 | von Gonten et al. | |
| 2003/0208465 A1* | 11/2003 | Yurko | G06F 19/322 |
| 2004/0008219 A1* | 1/2004 | Sarel | G06F 19/3487 |
| | | | 715/700 |
| 2004/0130702 A1 | 7/2004 | Jupp et al. | |
| 2004/0143512 A1* | 7/2004 | Sturr, Jr. | G06Q 20/20 |
| | | | 705/26.8 |
| 2005/0240880 A1* | 10/2005 | Banks | G06F 3/04817 |
| | | | 715/836 |
| 2005/0262119 A1* | 11/2005 | Mawdsley | 707/100 |
| 2006/0036472 A1* | 2/2006 | Crockett | G06F 19/322 |
| | | | 705/3 |
| 2006/0053470 A1* | 3/2006 | Colter et al. | 725/135 |
| 2006/0069603 A1* | 3/2006 | Williams | G06F 3/0482 |
| | | | 715/834 |
| 2006/0074321 A1* | 4/2006 | Kouchi et al. | 600/481 |
| 2006/0271421 A1 | 11/2006 | Steneker et al. | |
| 2007/0011146 A1* | 1/2007 | Holbrook | G06Q 30/0603 |
| 2008/0065419 A1* | 3/2008 | Esseiva | G06Q 50/24 |
| | | | 705/3 |
| 2009/0132963 A1* | 5/2009 | Morita | G06F 9/4443 |
| | | | 715/834 |
| 2009/0183106 A1* | 7/2009 | Dotson | G06F 17/30994 |
| | | | 715/772 |
| 2009/0192979 A1* | 7/2009 | Lunde | G06F 17/30943 |
| 2011/0125526 A1* | 5/2011 | Gustafson | G06F 19/321 |
| | | | 705/3 |
| 2012/0042283 A1* | 2/2012 | Tuesta | G06F 3/0482 |
| | | | 715/834 |

OTHER PUBLICATIONS

International Search Report and Written Opinion for PCT/US2009/46231, mailed on Jul. 23, 2009, 8 pages.

* cited by examiner

△ = Na 155. Consider ICU admission and
Hydration for hypernatremia and
Weight loss [Dehydration]

SYSTEMS AND METHODS FOR DATA AGGREGATION AND PRIORITIZATION

REFERENCE TO RELATED APPLICATIONS

This is a continuation-in-part patent application of co-pending application Ser. No. 12/156,723, filed Jun. 4, 2008, entitled "SYSTEM AND METHOD FOR DATA AGGREGATION AND PRIORITIZATION", which claimed one or more inventions which were disclosed in Provisional Application No. 60/933,038, filed Jun. 4, 2007, entitled "COMPASS". The benefit under 35 USC §119(e) of the United States provisional application is hereby claimed, and the aforementioned applications are hereby incorporated herein by reference.

BACKGROUND OF THE INVENTION

1. Field of the Invention

The present invention relates to systems and methods for the manipulation, presentation, and display of information. More particularly, the present invention relates to computer-implemented systems and methods which aggregate and prioritize data from any size data universe.

2. Description of Related Art

In the past twenty years there has been an explosion in the amount of information, and, more particularly, computer-accessible information made available to professionals in all fields. Especially in the medical field, key among the reasons for this explosion are more sophisticated and accurate testing techniques. Such techniques produce numerical and non-numerical measurements quantifying multiple parameters. Just a few years ago, many of the measurements now provided to professionals were unavailable. Because these measurements are easily transmitted using computer-based communication, there has been a tremendous increase in the amount of information provided to professionals in many fields of endeavor.

An unfortunate consequence of making large amounts of information available to professionals is that the finite capacity of human beings to absorb and to contextualize information may be exceeded, which may lead to adverse consequences. Important data may become buried in unimportant data. Some important data may even be inadvertently ignored. Signals of changes in data reflecting trends in the measurement of important parameters are missed. Valuable time is spent reviewing inconsequential background data. Missing key data or changes in data may vitally delay understanding the reasons for data distortions or data anomalies in key indicators. An additional problem is that often the software distributes the relevant data to many screens. A review requires many steps to examine the data. Another problem is that for many uses, the software system is defined and "read only" for the user. Any special concerns the user may have are not addressed by the software system. Yet another problem is that many reports are language-based rather than number-based, and automated systems do not identify critical results in text documents. A further problem is that often the user wants the data divided into two categories, namely "what I need to know now" and "what is not important to me". One user may find critical what another would not. A surgeon, for example, may want to see the data differently from an internist. Finally, simplicity of display decreases user fatigue. Currently, systems display a constant and significant amount of information as text, much of which may be of little or no interest to the user.

One example illustrating the problem of exceeding the finite capacity of human beings to absorb and contextualize information is in the treatment of patients by health care providers. Health care providers are given complex patient reports to read, analyze, and then, based on their analysis of the data presented, prescribe a course of patient treatment or therapy. Such a report on a particular patient may include personal information, test results, diagnoses, symptoms, and analyses on multiple pages in an arrangement that varies from patient to patient.

Current methods to identify critical results include identifying them by highlighting in red. Some systems place the critical reports at the top of the stack of reports for review. The reports are always presented as text. One conventional display of stacked test reports shows critical results highlighted in pink and abnormal, but not critical, results highlighted in yellow. A busy practitioner may be called upon to review many such arrays of medical information each day. A practitioner may also receive reports in different formats, including, but not limited to, electronically, on paper, or by facsimile. The location of the data categories varies from one system to another. Despite the effort spent reviewing each chart, the complex nature of a medical chart in combination with physician fatigue or time limitations may cause key information, such as a critical variance from a norm or a data anomaly, to be missed. The consequences of missing key items of data can be extremely dangerous or even fatal.

In addition to spotting a data variance from a norm, the professional must also be able to have a context for the data, which may require additional information from the particular patient's medical record to be able to prioritize the information to determine what may be the most critical of the variances from a norm and what, as opposed to other variances from a norm, may be less critical. Further, it would be advantageous to provide information regarding generally accepted interventions or therapy needed to respond to one or more critical variances from a norm.

Once a practitioner reviews a given report or set of reports, there may be a need for drug therapy intervention. If the patient has a unique condition or if the attending physician is not familiar with the use of some medications, the attending physician may have to consult a reference to select the correct medication. A critical variance from a norm or an anomaly in reported data must be identified, and a generally-accepted drug therapy intervention, if required, must be selected. The medical doctor must also be aware of any potential adverse consequences from recommended interventions, such as negative drug interactions.

In many situations, the aggregation of multiple sets of data, for example, from multiple patients, enables the discovery of characteristics of trends found in a larger universe of information revealed by observing multiple sets of data.

SUMMARY OF THE INVENTION

Computer-enabled systems and methods aggregate data related to a particular subject or field and present the data in a simplified display. The data is divided into predetermined categories which are graphically displayed in a predetermined arrangement. Systems and methods preferably differentiate and visually display critical data abnormalities separately from non-critical data, which prioritizes and displays further information regarding any critical data variances or anomalies and the recommended potential interventions to be taken in response to the variances or anomalies. The systems and methods enable an observer to identify the critical deviations or anomalies of data with respect to a predetermined base line by an intuitive visual display of all of the data from any sized data universe on a single screen. The data is preferably indexed at multiple display levels such as a stack of one patient's data, a stack of all patient data for the universe of patients of a single practitioner, or a group of practitioners of any size. In some embodiments, a portion of the display may be selected and expanded to show only that portion in greater detail.

In one embodiment, hovering the mouse over an area of interest, such as a critical result, causes the top result in the stack to be displayed. A click on the appropriate button reveals the entire data universe of the relevant patient in precisely the same format as in the original display. Another mouse click reveals the original stack again. The display of information is completely consistent in the location of data categories and its use becomes rapidly intuitive.

DETAILED DESCRIPTION OF THE INVENTION

Figure 1:
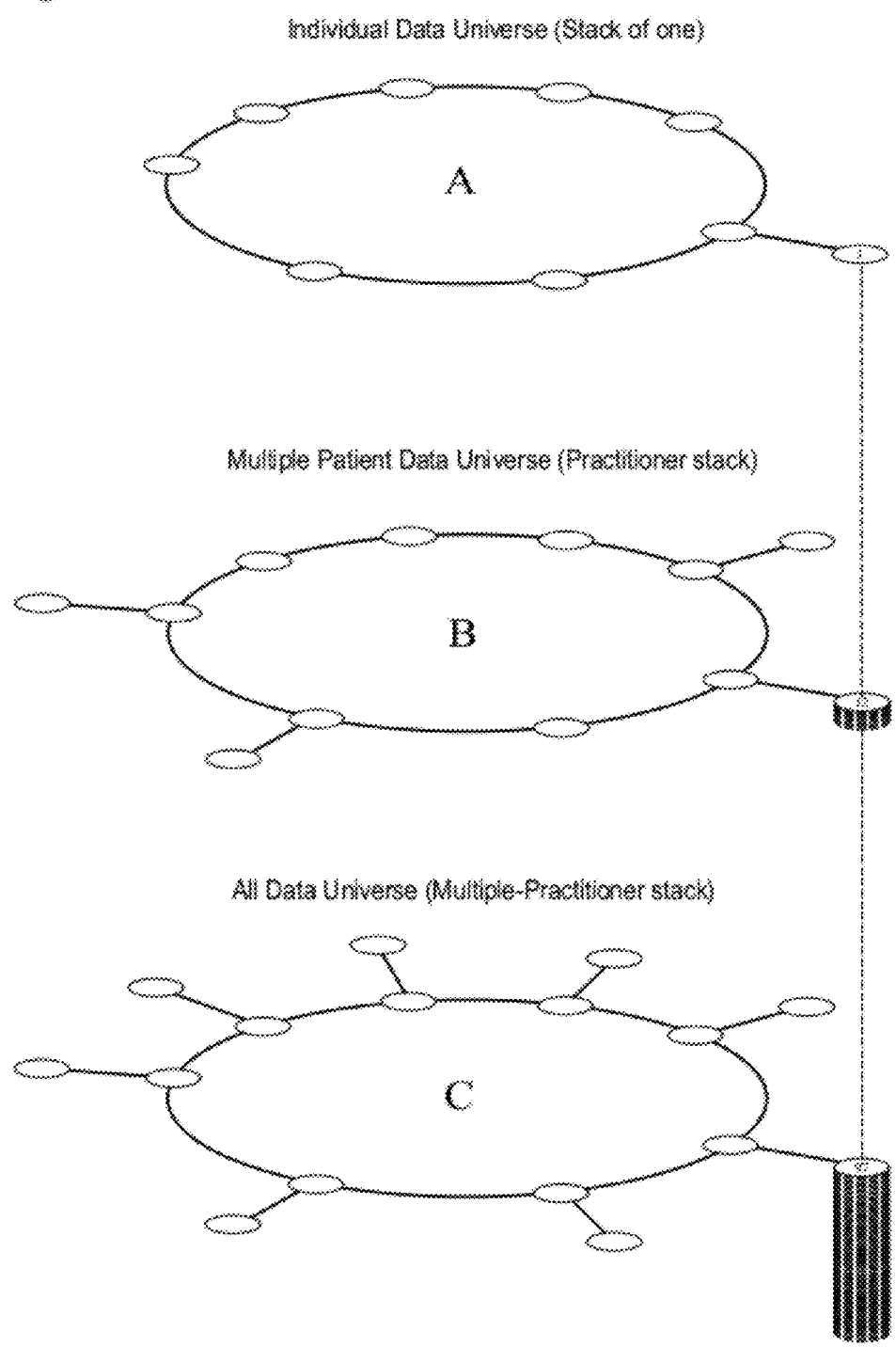
FIG. 1 schematically shows the relationship between display circles and related data, each small circle lying on the larger circle representing a data category and each circle lying outside the circle representing critical results for that data category, in an embodiment of the present invention.

Systems and methods for data aggregation and prioritization preferably include the use of a computer for aggregating data related to a subject, such as the health condition of a patient, and then for the division of the data into a predetermined group of categories. Each category of aggregated data is then graphically displayed initially at a predetermined position on a geometric figure, such as a predetermined coordinate point or range of points on the circumference of a circle. A circle is a preferred geometric figure in that it is also the shape of the human retina. The positional information in the display is thus preserved in the retinal image. Further, a certain category of data preferably always appears at the same point or range of points on the circle. This consistent positioning facilitates visual recognition by an experienced user. Specifically, if a user wants to observe a certain category of data, he knows exactly where to look for the desired data. These features all contribute to decreased user fatigue and thus decreased error frequency. More particularly, all data categories preferably have a distinct graphic address on a macro data array such as coordinates on a circular array, much like the directional positions on a compass.

In other embodiments, the system includes a granularity feature in that a portion of the graphical display may be selected by the user and expanded to show more detail within the selected portion. In these embodiments, a portion of the primary level display may be expanded as a secondary level display. As needed, a selected portion of the secondary level display may be expanded as a tertiary level display. The range of the expandable sections may be predetermined or may be user-defined. In some of these embodiments, the different display levels all have the same shape, but in other embodiments, each display level has a different shape, so that the user, once trained, may visually recognize what level of display is being shown merely by looking at the shape of the display.

Critical anomalies in the data are preferably graphically shown in an easy-to-read figure as variations from a norm and constitute a critical data anomaly. In other words, critical anomaly data is visually offset from similar non-critical data in the display so that the user can easily visually distinguish the data with critical anomalies.

The terms "critical" and "critically", as used herein, refer to results or numbers falling outside a predetermined range, referred to herein as a "normal" and "non-critical" range. The "non-critical" range includes both "normal" and "abnormal but not critical" results. In a medical context, in some embodiments, a result in the "critical" range alerts the professional to a potentially imminently life-threatening patient condition. In other embodiments, however, a critical result may not necessarily be life-threatening or require immediate action by the user.

The term "user", as used herein, refers to the individual viewing the displayed data using systems and methods of the present invention. In some embodiments, the term "professional" is used interchangeably with the term "user", but in any embodiment, the user may be a non-professional as well, including, but not limited to, the patient or an individual with proper clearance to access the data.

The system preferably can display aggregated data categories of even infinite complexity in progressively greater levels of detail or specificity on a single screen. At its most granular expression, this indexing function displays the maximally specified data type of interest. This allows a user of the system the option to look at a visual display representing all of the data in the universe at once or only the data associated with one or more index options.

Thus, systems and methods organize and present information such that an experienced user knows just where to look for a particular piece of information and is quickly able to identify any problems that need to be addressed or corrected. An additional important feature of the circular display is its simplicity. The circular display graphically presents the data in as simple of a manner as possible while still meaningfully grouping the data and without restricting access to the full details of the data. A circular display is preferably ALWAYS visible on the screen and preferably only takes up a portion of the screen such that the user can access and display the desired details while still being able to view the circular display as a point of reference. The system preferably electronically enables the display of an entire data universe on one screen possibly containing at least one critical data icon. Selecting the critical icon calls up the subsidiary universe of the individual data universe. Intermediate universes of complexity between those of the entire data universe and the individual data universe also exist. An example of an entire data universe might be all the medical data of medical patients in an entire medical practice. The individual medical universe would be the data of a single patient. An intermediate data universe would be that of the universe of patient data for an individual practitioner. With a single click, the user may "toggle" among different stack sizes, for example, a single patient, a single practice, or all practices. The user thus has a consistent context of his data universe. Clearly, the categories "entire" data universe, "individual" data universe, and "intermediate" data universe have application in any field as well as in medicine.

The complete display preferably creates a visual macro indication of the subject data, including a visual indication of the existence of any data critically outside the predetermined range. The computer-created display preferably provides a link to a micro display of the data using a visual indication of the data that falls outside of the acceptable range (normal and non-critical abnormal). Default critical parameters may be set by the electronic medical record (EMR) system, but they may additionally be adjusted by the user on the fly. Revision of the criticality standard by the user preferably causes the computer to re-evaluate all of the relevant data, reapportion the data between normal and critical, and update the circular display accordingly. In some embodiments, the system allows the user to define a new parameter, such as a comparison of two pieces of data, with a user-defined change qualifying as a critical result. For example, a significant drop in blood count for a particular patient from a prior level may be critical even though neither level itself is critical. The data stack size of one display preferably further describes the data identified on a larger stack size display of the data describing the subject. The display of multiple sets of provided data may additionally be aggregated to enable the discovery of information characteristics and trends found in progressively larger universes of information revealed by observing multiple sets of data.

An alternative embodiment of the display shows the history of interventions previously made along with additional information describing recommended interventions according to a predetermined priority. More particularly, the system and method preferably provide a layering of data starting with a macro data array such as a data array on a circle. In some embodiments, the next layer of data display provides greater detail of a portion of the data set, such as the data in one quadrant or one arcuate sector of the initial circular display. This display embodiment may include a feature by which the user demonstrates and records an acknowledgment of having observed certain key portions of the data. Another layer of data display may provide an historical or time-expanded display of the parameters shown in a data display having more detail, such as a quadrant of the initial circular display.

As explained above, professionals in numerous fields are provided with multiple reports including data reporting measurements or test results including numerous parameters. The data in the reports may be used to represent the condition of a particular parameter along with a history of the work done or interventions made by others. The professional evaluating the reports is then expected to use professional judgment to determine if the data warrants action or intervention or if a future course of action is necessary before an intervention is made.

In most cases, the judgment of a professional is needed because the data reporting measurements or test results including one or more parameters show what may be called baseline data and other data that may be called intervention data. Baseline data typically expresses or confirms test results within a normal or anticipated range of values. Intervention data is that data which shows a critical deviation of data from a norm or a data anomaly. If a critical data deviation from a normal result or an abnormal but not critical result is shown, some type of intervention may be needed to address the deviation of data. The proper management of critical situations, once detected, is usually straightforward. Proper intervention may be a prescribed course of action, or alternatively proper intervention may be verifying test data, particularly when there is an unpredicted or unusual data anomaly. In other cases, the data reporting measurements of one or more parameters may be indicative of a trend for which intervention may or may not be needed. The trend, however, may be indicative of a potential for some other situation recognizable by the professional as requiring additional testing or more frequent testing.

Those professionals called upon to exercise professional judgment must determine if deviation of data from a norm or a data anomaly represents a situation in which known interventions provide predictable results. Many of these interventions are generally accepted by professionals, but other less well known situations may require research or further study on the part of a professional. The system preferably accommodates customization such that the professional may adjust the parameters for criticality to suit their own needs or their own area of practice. Still other interventions may trigger unanticipated complications which might exacerbate a measured condition.

Detracting from the ability of a professional to exercise professional judgment are two key factors. The first factor, as explained above, is the finite ability of a human being to absorb and contextualize data. In many fields, the professional is presented with so much information that important deviations from a norm or anomalies in data are potentially masked by being buried in other data.

When treating a patient, a medical professional, more particularly a physician, is presented with information about a patient in various forms. Much of the data presented to a physician is in the form of numbers produced by direct measurement or lab tests. While laboratories providing measurements or test results may indicate if a particular measurement or test result is outside of a "normal" or "abnormal but not critical" range, the out of range measurement or test result may easily be misread or completely overlooked when a physician has only a short period of time to review numerous complex reports listing the results of various measurements and tests, such as blood tests and urine tests.

Display of Critical Results

In a preferred embodiment, the data display shows the data for any data universe displayed around a circle. The display in this embodiment is simple. All and only critical results are displayed outside the circle. Data is distributed to categories around the circle. FIG. 1 schematically shows display circles with the smaller data category circles being distributed around the edge of each display circle and any smaller circles located off the display circle representing critical results. The display circles in FIG. 1 appear as ellipses only because of the perspective from which they are being viewed in FIG. 1.

Figure 2A:
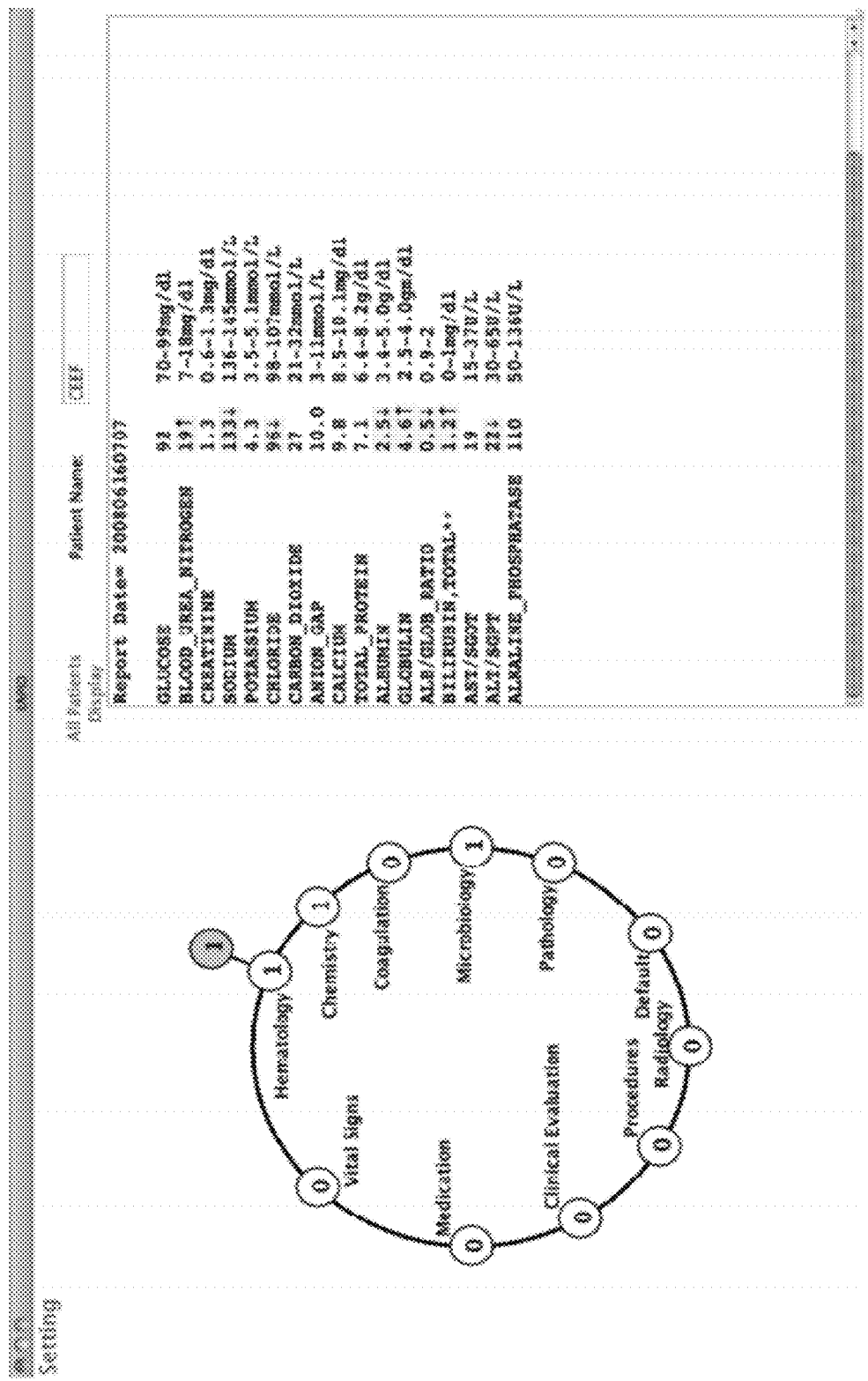
FIG. 2A shows a screen shot of a display layout graphically presenting data at a level of a single patient, corresponding to Circle A of FIG. 1, in an embodiment of the present invention.

FIG. 2A shows patient data for a single patient (CEEF). One portion (the left portion in FIGS. 2A-2C and 3) of the display area presents the display circle. Another portion (the right portion in FIGS. 2A-2C and 3) of the display area presents the details of a specific test result or other medical data. The prioritized representation of the data, as shown in the left portion of FIGS. 2A-2C and 3, preferably persists on the display screen as a point of reference no matter what the user is reviewing in the other portion of the screen. The display preferably represents all data for one of the patients for which the health care professional is currently responsible. The display allows the professional to prioritize his review of the data. Each type of data is preferably grouped with similar data types, such as the labeled types in FIGS. 2A-2C and 3. The numeral in each circle in FIGS. 2A-2C and 3 represents the number of different reports to review of each type. The numeral in each smaller circle on the perimeter of the primary circle represents the total number of unreviewed reports of that type that the health care professional needs to review.

Each type of data preferably always appears on the same location of the display circle, regardless of the data universe being displayed. In FIG. 1, data is shown at the same location in the physician group data universe display, the professional data universe display, and the patient data universe display. In the case of FIG. 1, the patient only has one data category with a critical result (FIG. 1, Circle A), whereas the professional has four data categories with critical results (FIG. 1, Circle B), and the physician group has eight data categories with critical results (FIG. 1, Circle C).

Figure 2B:
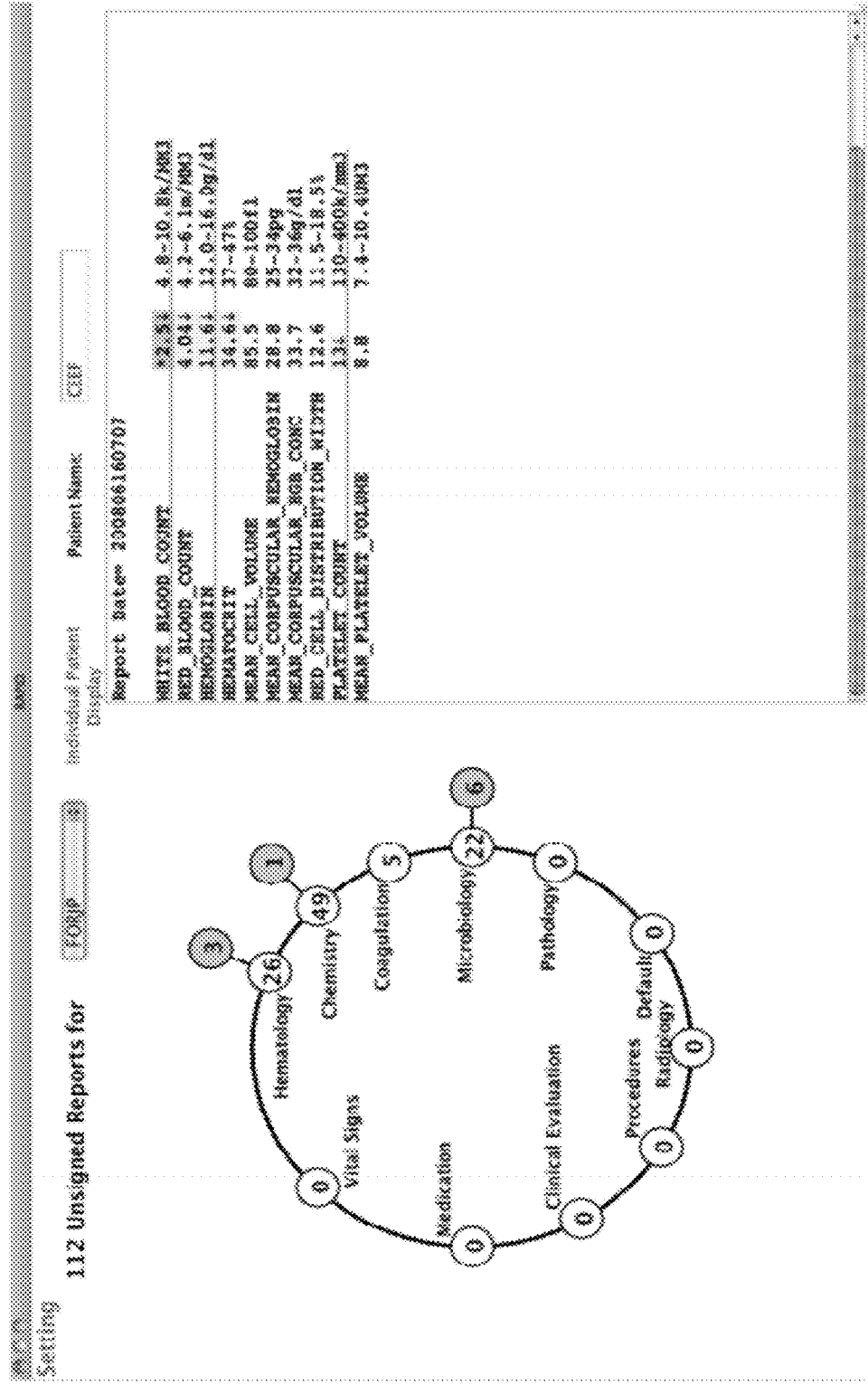
FIG. 2B shows a screen shot of a display layout graphically presenting data at a physician level, corresponding to Circle B of FIG. 1, in an embodiment of the present invention.
Figure 2C:
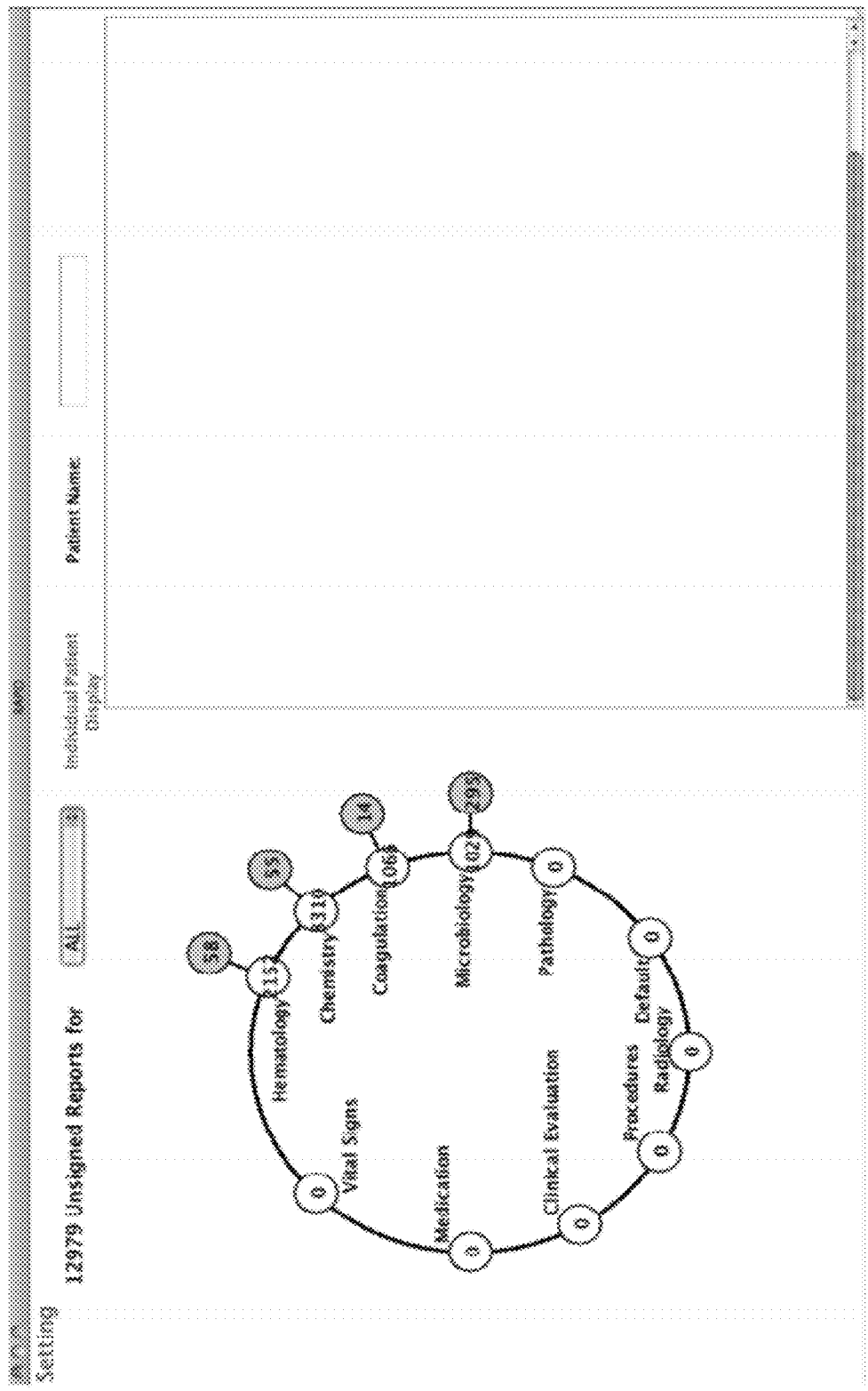
FIG. 2C shows a screen shot of a display layout graphically presenting data at a physician group level, corresponding to Circle C of FIG. 1, in an embodiment of the present invention.

Similarly, data is shown at the same location in the physician group data universe display of FIG. 2A, the professional data universe display of FIG. 2B, and the patient data universe display of FIG. 2C. In the case of FIGS. 2A, 2B, and 2C, the patient only has one data category with a critical result, whereas the professional's patient population includes three, and the physician group has four data categories with critical results. The right portion of the display window shows specific sets of test results for a patient in FIGS. 2A and 2B. In the display shown in FIG. 2C, because a stack from the display circle has not been selected by the user, no test results are shown in the right portion of the display.

Figure 3:
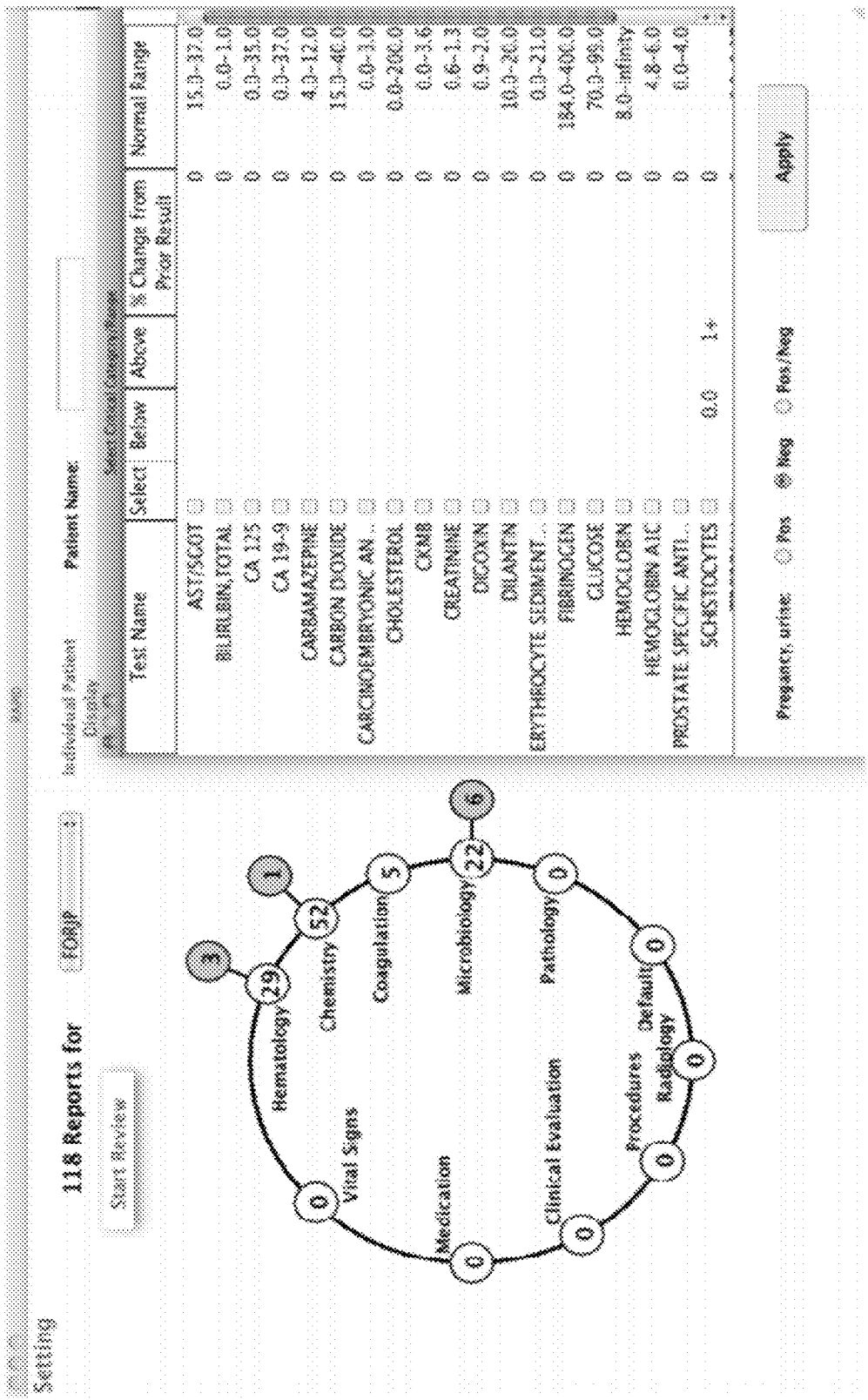
FIG. 3 shows a screen shot of a display layout presenting a drop down screen displaying system or default critical parameters and also user-defined critical parameters in an embodiment of the present invention.

If there are any critically abnormal results or data in the report, such as the case for Hematology, Chemistry, and Microbiology reports in FIG. 3, additional circles outside the primary circle show the number of such unreviewed reports. The critical circles may be colored, such as, for example, red, or shaded, as in FIG. 2A, to draw the professional's attention to them. This allows the professional to give priority to the critical results and review them first. In the case of the screen shown in FIG. 2A, the professional has three reports to review for patient CEEF. Rather than carefully reviewing each of the three reports for critical abnormalities and not knowing whether each report may or may not include a critically abnormal result, the professional can quickly and selectively review the one critical report first and address the critical abnormalities as necessary. Once the professional reviews the critical report, the normal report can be reviewed more quickly and with less of a sense of urgency and heightened awareness. As in previously-described embodiments, the professional can preferably select critically abnormal reports, and once the professional signs off on a particular report, the numerals in the circles are updated and the reviewed report is removed from the queue. Reports, within a specific stack of similar reports, may be prioritized by the system, such as by the age of the report with older unreviewed reports receiving a higher priority.

FIG. 2B shows the clinical results for all of the patients of a practice. This display appears with clicking "all patient display". By clicking "individual patient display" all the data in the practitioner's practice appears.

With reference to the display of FIG. 3, the system is preferably personalizable by the user. More specifically, the system preferably permits the user to change the critical range for any parameter or to define a new parameter, including, but not limited to a parameter that is a ratio of two parameters already in the system, a parameter that is a change over time of a parameter already in the system, or a parameter that is calculated by a user-defined equation, where all of the variables in the equation are parameters already in the system. In some embodiments, the "critical range" is a list of words or phrases, which trigger a piece of data containing one or more of these words or phrases to be assigned a critical status. In these embodiments, the user may add or remove one or more of these words or phrases from the critical list. The process for changing the critical range is preferably intuitive and may be implemented in a number of different ways within the spirit of the present invention. In some embodiments, the critical range may be changed by the user by a selection, such as by a mouse click or by moving a cursor, of the test name, the test result, or the displayed range, which may or may not be the critical range criterion used by the system. Such a selection may open a display, such as that shown on the right side of FIG. 3, that permits the user to change the critical criterion only for the selected data, only for the selected data type, or for any of the current critical criteria in the system.

In the embodiment shown in FIG. 3, the display lists the test names alphabetically with the normal range in the system listed for each test in the far right column. The user may change the critical range for one or more tests by selecting the check box next to the test name, which allows the user to re-define the critical range by entering a "Below" value, an "Above" value, or a "% Change from Prior Result" value, and then selecting the "Apply" button to apply the new range. In FIG. 3, the critical range for the Schistocytes test has been changed to below 0 or above 1. The system may allow the user to change the range by typing in new values or by using arrows or the mouse to increase or decrease the upper or lower ends of the non-critical range. In some embodiments, a user selects a portion of the display, such as a button, which allows the user to change one or more critical range criteria. In some embodiments, multiple changes to the system critical ranges may be implemented at the same time. In other embodiments, the user is able to make critical a change from a prior result of a significant degree or percentage that may indicate a critically deteriorating situation (for example, a hemoglobin level falling from 12 to 8).

In some embodiments, the user may define whether or not the change to the system critical ranges is applicable to only some of the data in the system, such as for one or more specific patients. In other embodiments, the change is applied only to the data accessible by the user making the change to the system. In other embodiments, the change is applied to all data in the system.

When the user changes one or more critical range criteria, the system preferably immediately re-evaluates all of the data accessible by the user to re-prioritize abnormal results. In some embodiments, when the user criteria are different from the system's default criteria, the system still alerts the user in some way to critical results according to the system's default criteria that are no longer critical results by the user's criteria in the case that the user mistakenly has changed the critical range or changed it to a range different from what the user intended to change it. In other words, in some embodiments the EMR system default critical ranges can not be deselected either intentionally or inadvertently.

In many cases, the data is quantitative and the system identifies critical data by comparing numerical data to a critical range of numerical values, but in some cases, the data is a written summary with qualitative results and no numerical values. In some embodiments, the system is able to use "natural language" to identify critical results in the text of a document, such as a test report. In these embodiments, the system may scan text to identify predetermined terms, such as "new mass" or "adenocarcinoma", which triggers the system to assign a critical status to the data.

In some embodiments, when viewing a report for a particular patient, the professional may select a "Patient Information" button, preferably located below the test result window. This button links the professional to the patient's full medical record in the system with the patient's display circle being shown in the left portion of the screen. Another button preferably allows the professional to go back to the professional's display circle. In some embodiments, an "Order" button, preferably also located below the test result window, provides a link to where the professional can order further tests or prescribe medication for that patient. In such embodiments, the system is preferably integrated with an EMR (electronic medical record) system so that the ordering professional is able to include patient-specific comments with the order. When the professional believes that a prescribed medication may be necessary to treat the patient, the system preferably alerts the professional to any allergies and any interactions with other medications currently being taken by the patient that would make the new medication dangerous to the patient. The professional may also have access to a prescribed medication database in the system, which may alert the professional to known side effects of the medication and to any alternative medications that may be used to treat the patient's condition.

To demonstrate the ability of systems and methods to aggregate and prioritize data, publicly-available medical data from two different databases, namely Orchard and Meditech, were combined, and by methods and systems of the present invention, were categorized, indexed, and displayed. It was then determined to be possible to review all of the critical results from the data in a fraction of the time it would take a professional to review the same data presented in the conventional way.

Although for simplicity of display, visualization, and review, reports are preferably only either characterized as normal/non-critically abnormal and critically abnormal, in some embodiments, results that are not in a predetermined normal range may be further separated, such as between critically abnormal and non-critically abnormal, with some appearing inside the primary circle and some appearing outside the primary circle or all appearing outside the circle at different distances from the primary circle perimeter.

Data Stacking Function

In one embodiment, each piece of data is associated at least with an individual and with a professional responsible in some way for the data associated with the individual. In this embodiment, the professional is typically responsible for more than one individual in the system. The stacking feature allows the professional to look either at all data in the universe regardless of the data association, only the data associated with the professional, a different professional, or a group of professionals, or only the data associated with the individual. In another embodiment, each piece of data is associated with a date related to the data, and the indexing function allows the user to look either at all data regardless of the associated date or only the data associated with either a predetermined or user-defined date or range of dates.

In some embodiments, the data is indexed by one or more status identifiers. In one embodiment, the status identifier is whether the data has been reviewed, such as by a professional responsible for reviewing the data, or is unreviewed. In this embodiment, the indexing feature allows the user to view either all data in the universe regardless of review status, only the reviewed data, or only the unreviewed data.

Expansion of the data universe from the data of a single patient (stack of one, FIG. 1, Circle A) to the data of a single practice (FIG. 1, Circle B) to the data of a group of practices (FIG. 1, Circle C) is shown in FIG. 1. In the embodiment as represented in FIG. 1, the dashed circles below the numbered circles represent each of the reports in that stack and are shown for illustrative purposes only. The one critical result from Circle A is also found within the stack of 12 in Circle B and the stack of 97 within Circle C. The professional's display circle is linked to other display circles related to the professional's display circle, as shown schematically in FIG. 1. The universe of interest (see FIG. 1) is selected by the user. By way of explanation schematically in FIG. 1, if the practitioner selects the data stack of one (FIG. 1, Circle A), he displays the universe of a single patient.

This display would be available to a nurse caring for the patient of Practitioner A. With a single click the user toggles to the data for all of his patients (FIG. 1, Circle B). This practitioner level display is also used by Practitioner B covering Practitioner A's patients on the weekend, for example. The practice manager or insurance company, however, may want to view all data in the system (FIG. 1, Circle C).

Although FIG. 1 shows data display at the patient level, at the practitioner level, and at the universe level, the data universe may be sortable in any way into any level of data display, including user-defined levels. Each data value is preferably associated with multiple indexing features related to the data value. In one embodiment, in addition to being sortable by the patient, the practitioner, and the practice, each data value is associated with additional indexing features related to the data value, such as, but not limited to, date of the test, age of the patient, residence of the patient, occupation of the patient, and gender of the patient. In this manner, when a user wants to look for other critically abnormal data values associated with indexing features similar to the indexing features for a particular critically abnormal data value, the user may look at potentially relevant indexing features associated with the particular critically abnormal data value and then create a user-defined level of data display to see if other similar critically abnormal data values are in the data universe with the same indexing feature in common. As an example, the user sees test results for a patient showing a critically abnormal data value for liver enzymes. The patient's record shows that the patient is a 42-year old male. The user then enters male for gender and 40-45 years for patient age. The system then filters through the data universe and displays a data display with only data associated with male patients between 40 and 45 years of age. The user may then check the filtered data display to look for other examples of critically abnormal data values for liver enzymes.

The practitioner level screen of FIG. 2B would be the typical starting point for practitioner review. The user's display circle for an individual patient CEEF in this case includes a critical abnormality of a hematology test result. When viewing patient CEEF's test result, the professional can toggle "all patient display" to view the patient's other records. The user may be able to access other display circles, such as a display circle for the physician group where the professional works.

FIG. 2C shows a display circle for all 12,979 of the unsigned reports for the entire data universe. By selecting or typing his name in the "ALL" portion of FIG. 2C, the display circle is modified to shown only the 112 unsigned reports for professional FORJP, as shown in FIG. 2B. Furthermore, the user may select the patient CEEF to change the display circle to one showing only the data for patient CEEF, as shown in FIG. 2A. In some embodiments, the patient level data circle includes all data in the system for the patient, not just the unsigned/unreviewed data.

Typically a practice manager or insurance reviewer would display the screen shown in FIG. 2C. The system may also include billing and insurance data, which may be accessed by certain care center staff and insurance company personnel as appropriate. This data may also be linked to other data in the system, when relevant, and accessed through one or more display circles.

In some embodiments of the present invention, the set of extreme anomalies from infinitely complex data sets is preferably localized on a single display, such as a circle.

In another embodiment, the systems and methods allow all data in a universe to be displayed in a circular indexed format where subcategories or fractals of data may be displayed on subordinate images. The data sets within a circle are actually a number of superimposed circles. The data anomalies become evident for a single data set, such as for a single patient, within a data universe, such as the patient data for a single practitioner or group of practitioners. This allows a practitioner to immediately see, from his entire practice, the data with critical abnormalities requiring immediate attention.

Index of Data Categories

In another feature of the present invention, instead of stacking the same type of data such as described above, the index function allows the display of more general or more specific data categories.

Figure 4A:
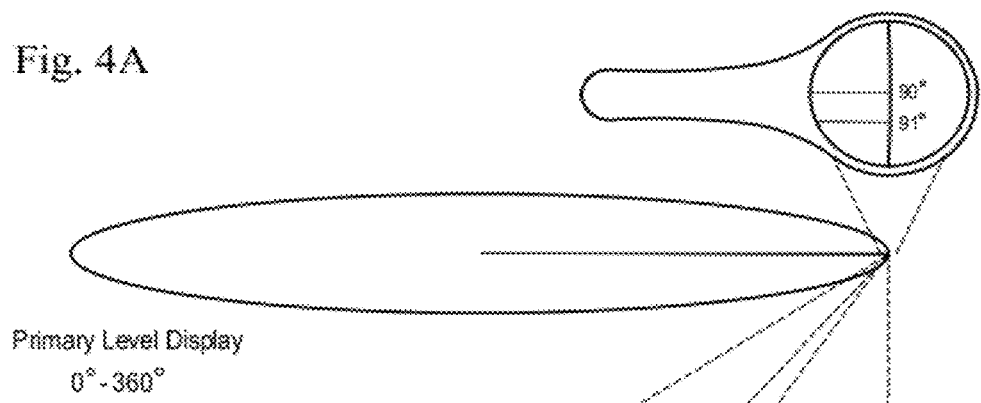
FIG. 4A shows a schematic representation of a primary level of data categories in an embodiment of the present invention.
Figure 4B:
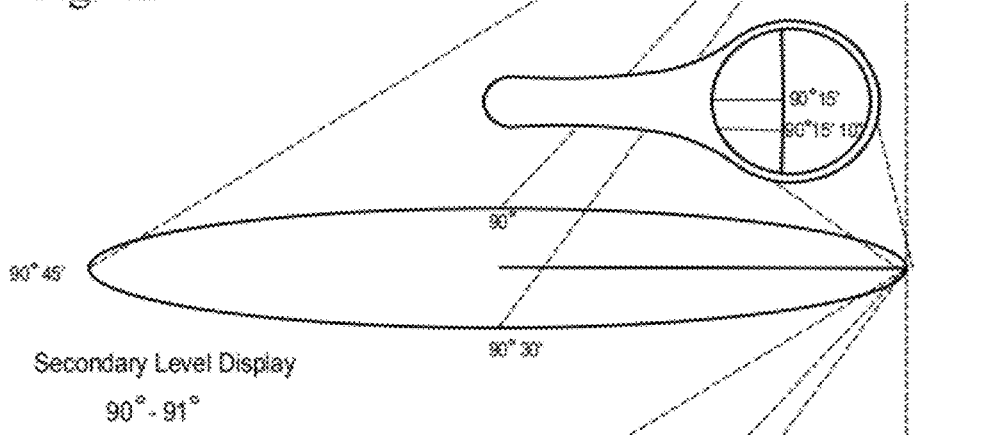
FIG. 4B shows an expansion on a secondary level of data between 90 and 91 degrees of the 360 degrees of FIG. 4A.
Figure 4C:
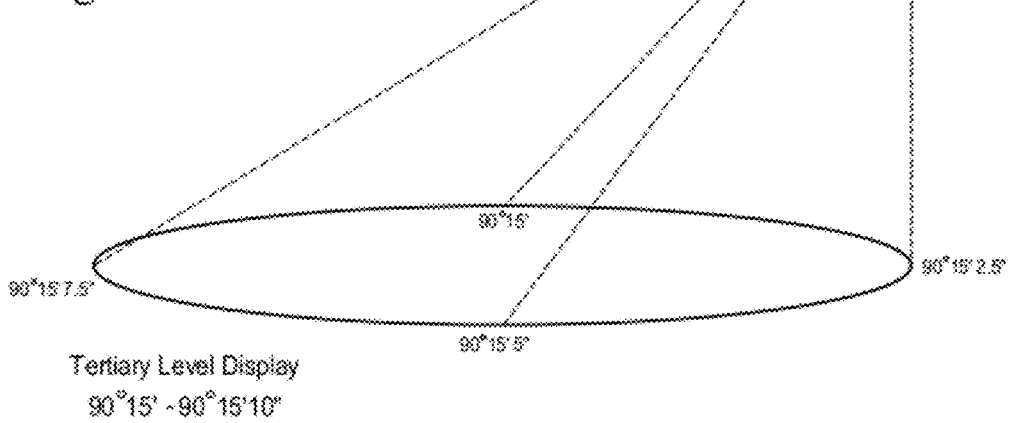
FIG. 4C shows an expansion on a tertiary level of data between 90°15'0" and 90°15'10" of the degree of FIG. 4B, again representing a 360-fold amplification.

In some embodiments, multiple layers of decremental fractals of the display are used to display the data of any sized data universe progressively more granularly rather than as more results of the same data categories, as shown schematically in FIGS. 4A through 4C. In these embodiments, data is presented in a most general manner in a primary circular display (FIG. 4A). The decremental fractal levels in FIGS. 4B and 4C may also be circular as in the previous embodiments. The display circles in FIGS. 4A through 4C appear as ellipses only as a result of the perspective view of the figures. Alternatively, each display level may have a different shape, as in the case of FIG. 6B, so that the trained user may visually recognize what level of display is being shown merely by looking at the shape of the display. By selecting a section of the primary display (FIG. 4A), the user directs the system to show a secondary decremental fractal (FIG. 4B) with greater details of only the data of the selected primary section. Even greater details may be viewed in higher-order displays, as needed, such as the tertiary decremental fractal shown in FIG. 4C. The size of the sections and number of orders of displays may be predetermined based on the amount and complexity of the data to be presented. In FIG. 4A, the primary display circle is divided into 360 one-degree sections. Each one-degree section of the primary display circle (FIG. 4A) expands into a degree fractal display circle with 360 one-degree sections. Each one-degree section of the degree fractal display circle (FIG. 4B) expands into a further degree fractal display circle with 360 one-degree sections. Thus, this data structure, increasing to the base 360, has 360 primary sections, 129,600 secondary sections, and 46,656,000 tertiary sections. In some embodiments, different displays may have different numbers of sections in order to customize the display based on the amount and types of different data at each level.

The data universe is rendered as a coordinate on a circle representing n-dimensions of data (see FIG. 4A). The data within the data universe at location 90°-91° is expanded by a click and distributed according to a predetermined or user-defined rule (such as alphabetically) around a subordinate or secondary level (see FIG. 4B). A further subordinate data universe at location 90°15'-90°15'10" is expanded and distributed as a tertiary level display (FIG. 4C). This may be visualized by "cutting" the circle and collapsing the resulting line segment at a coordinate of a circle representing n-dimensions of data. The image at the coordinate preserves all the upward or downward anomalies present on the entire original circle. For example, suppose that position 90-91° as in FIG. 4A includes the category of anemia. FIG. 4B at position 90° 15' may include anemia in adults due to vitamin B12 deficiency. FIG. 4C at 90° 15'09" may include clinical vignettes of worldwide reports of patients with vitamin B12 deficiency similar to the patient whose data is being displayed (e.g. a 45 year old woman with anemia after gastric by-pass surgery and breast cancer).

Additional Features

In some embodiments, when a critically abnormal result is entered into the system, one or more electronic messages are simultaneously sent to the responsible professional or professionals to alert them to the result. The electronic message may be in any form, including, but not limited to, a pager message, a text message, a phone call, an instant message, a voice message, an intercom or speaker announcement, or an electronic mail message. The electronic message is preferably automated but may alternatively be sent manually. In some embodiments, a follow-up message is sent if the critical result is not marked as reviewed in the system within a predetermined amount of time.

In a preferred embodiment, the above-described embodiments are implemented as part of a larger system of health care management. Such a system may be used on a medical practice level or a hospital level, but most preferably, the system is used on a level, such as a state or national level, such that each patient health profile is comprehensive of that patient's medical history and current medical status. In such a system, the comprehensive health profile of each individual in a system is preferably maintained electronically in a database. Although electronic records for different individuals may be stored in different physical locations the electronic record for each individual is preferably remotely accessible to any health care professional with clearance to view that individual's medical records. In some embodiments, the remote access is web-based.

In such an embodiment, maintenance of the security of an individual's medical information is of great importance. Preferably this security is achieved by providing different health care professionals with different levels of clearance to different information. Secure access to the system may be provided to an individual health care professional in a number of different ways. Each professional has his or her own individual account, which provides the professional with access only to the medical records for which the system has received authorization to provide to him or her. In some embodiments, data is displayed on a lap top computer. In other embodiments, data is displayed on a desk top computer. In some embodiments, access is provided via entry of a personal login or password. In other embodiments, an electronic card held by the professional identifies the professional to the system. The system preferably includes an automatic logout mechanism such that the system remains secure in the case of the professional forgetting to actively log out of the system when finished reviewing information in the system.

Some medical professionals may have one-way access to the system in that they can add data to an individual's medical profile without having access to view any other information in that individual's medical profile. Alternatively, however, many medical tests are now automated, and data entry and updates to an individual's health profile is preferably automated, whenever possible. In such cases, the technician in charge of running a particular test, such as a blood test, does not need to be able to access the individual's medical profile in order to add the test results to that profile. In some cases, however, the test is not an easily quantifiable test, and the results must be viewed by a specialist, such as an x-ray by a radiologist, before being added to the medical profile of the individual. In such cases, the specialist may update the individual's medical profile by providing qualitative results of the test to the system database.

In some embodiments, the system is tied in to billing and health insurance claims. In these embodiments, billing information may be provided automatically to a billing department, and health insurance claims may be sent automatically to the relevant health insurance entity for the patient.

In another embodiment for use in a setting such as an emergency room or a hospital, a system using data displays, such as the one in FIG. 2B, also includes a mechanism by which responsibility for a patient or responsibility for review of certain data or test results is transferred from one health care professional to another, such as at the end of the first health care professional's work shift.

Alternative Embodiments

Figure 5A:
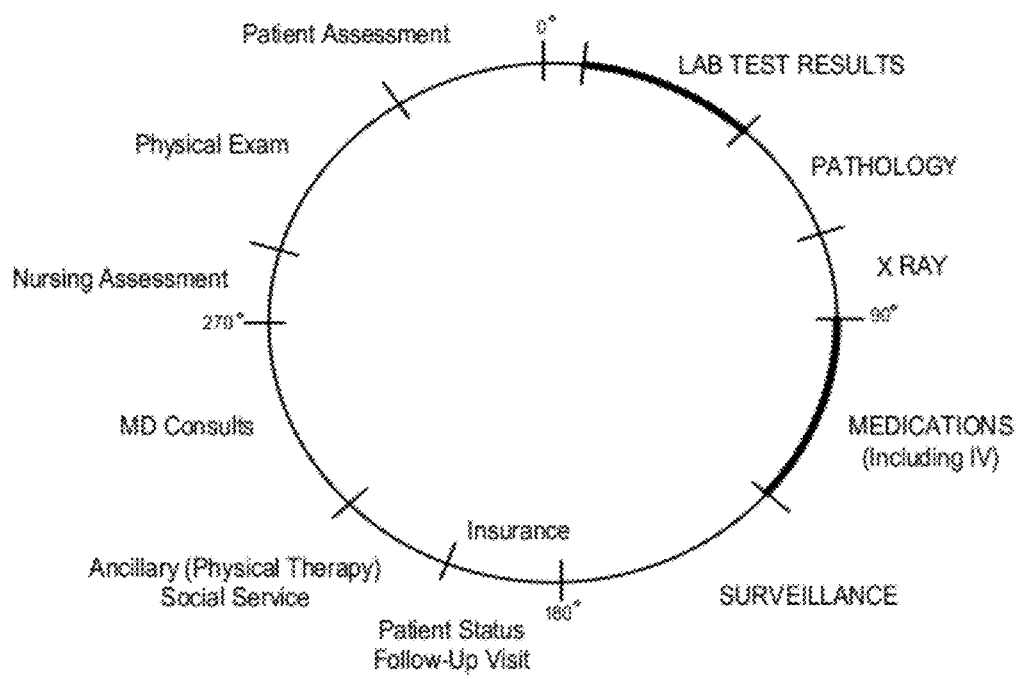
FIG. 5A shows a display layout for data aggregation in an embodiment of the present invention.

According to one embodiment of the system and method, data typically reported on the health condition of a patient is arrayed as shown in FIG. 5A. FIG. 5A shows schematically a display interface of a substantially circular geometric figure around which has been arrayed various types of information relating to the health condition of a patient and the medical care being provided to the patient. A circle, the geometry of the human retina, is shown as being exemplary of a graphic representation of what the system and method of the present invention presents to a user. In other embodiments, a one-dimensional shape, such as a line, may be used. In yet other embodiments, another two-dimensional shape, such as an oval, a triangle, or a rectangle, may be used without departing from the scope of the present invention. In yet other embodiments, a rotatable two-dimensional representation of a three-dimensional object, such as in computer-aided design (CAD) drawings, may be used. The circumference of the circle or the perimeter of the selected figure preferably indicates a normal condition. If a normal condition can exist over a range of numbers, portions of the circumference of the circle may be a thickened line as shown in FIG. 5A. The circle is chosen as an exemplary embodiment, because positions around a circle are easily described by coordinates. Each specific type of data preferably has its own specific coordinate. Such positioning enables a user to quickly identify, in terms of location on the circle, the type of data that is critical, and this is preferably shown as a radial line or ray extending above or below the circle.

Surrounding the circle shown in FIG. 5A is a predetermined array of information categories. Specifically, proceeding clockwise around the circle, the first approximately 45° arc is designated for the display of lab test results. Next is an approximate 30° arc designated for showing pathology test results. Completing the first 90° of the circle is another small arc on which information regarding x-rays is displayed. Proceeding further around the circle along the next approximately 45° arc are those medications being administered to a patient. The medication arc is followed by a surveillance arc of approximately 45°. Shown in the surveillance arc will be such activities as a vaccination or a mammogram.

The next approximately 90° arc moving upward from the bottom or 180° degree position of the circle is a patient history sector to include the patient status and information such as physical therapy, work by social service agencies, and consultations with other physicians. The last 90° arc proceeding to the top of the circle from the 270° degree position is for patient assessments including, but not limited to, a nursing assessment, a physical exam, and an overall patient assessment. The same information preferably appears at the same location on the circular display of measurements or test results for every patient. After a short period of use experience, the physician using the system and method is able to focus on the information describing the health condition of a patient without the need for the display identifying labels positioned around the circle. Thus, for simplicity and for ease of viewing the label portion of the screen shown in FIG. 5A, the identifying labels may be turned off or on as needed for training or verification purposes.

The array of medical information graphically representing test results as shown in FIG. 5A is suggestive only to illustrate the operability of the system and method of the present invention. A utility of the system and method would be if a medical care improvement agency, for example a medical practice specialty board, were to standardize the format for the graphical array health of care information in a particular practice area such as internal medicine, surgery, or urology.

Figure 5B:
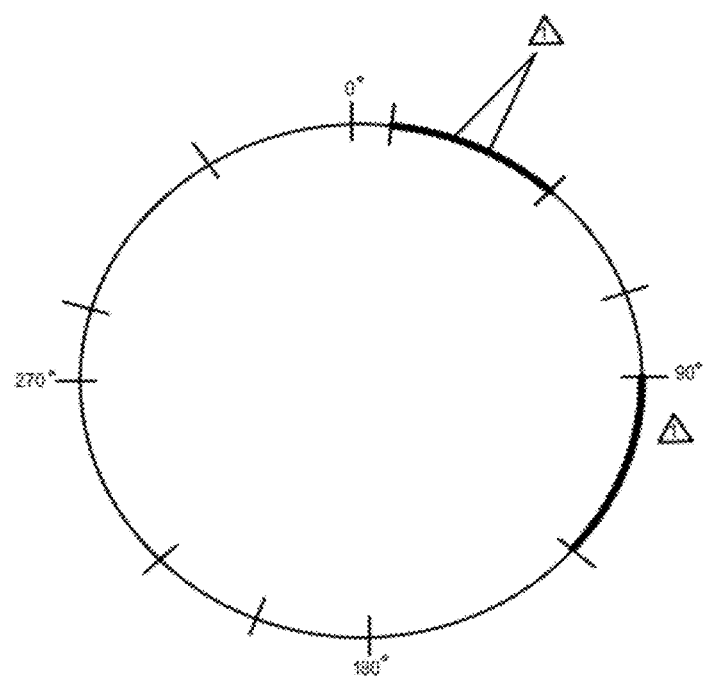
FIG. 5B shows a first display of individual test report critical deviations with regions of interest in bold using the layout of FIG. 5A.

FIGS. 5B through 5F show different data display embodiments for individual test report deviations from a norm along with an explanatory note further describing the individual test report deviation from a norm or suggesting a potential intervention. FIG. 5B is illustrative of a first screen, where a single critical result is shown. This critical result is highlighted by the numeral "1" in a triangle. Note by comparison to FIG. 5A that numeral "1" in a triangle appears in two sectors, one relating to lab test results and the other relating to medications. The explanatory note at the bottom of the screen indicates that the reason for the appearance of the "1" in a triangle is that the test result for sodium (Na) levels is abnormal. That is, the reported amount of sodium (Na) is critically above or below the normal range. The severity of this critical result is reflected by the height of the triangle including the numeral "1" from the perimeter of the circle at about the 20° location. In the note at the bottom of the screen display, a suggestion is made that an intervention described as "Consider IV Hydration" is recommended as a therapy in response to the test result illustrating data describing the patient's high sodium condition.

Figure 5C:
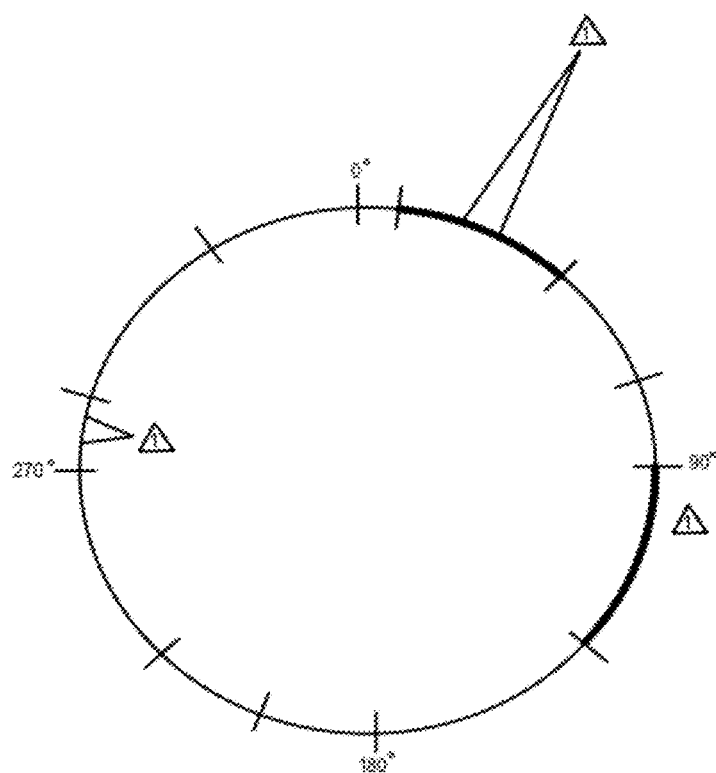
FIG. 5C shows a second display of individual test report critical deviations using the layout of FIG. 5A.

A similar situation is shown in FIG. 5C. Note here that the level of sodium sensed is much higher than in the case of FIG. 5B, as shown by the greater distance of the numeral "1" in a triangle at about the 10° location. Note also that a second and third numeral "1" in a circle appears at the 90° position and just above the 270° position in those portions of the circle identified, according to FIG. 5A, as being for medications and the reporting of physical exam information, respectively. As indicated in the note positioned just under the circle, the sodium level test result is reported as being 155. A sodium test result of 155 indicates a critical condition, thus triggering a message recommending the admission of the patient to an ICU as well as hydration for the treatment of hypernatremia and weight loss.

Figure 5D:
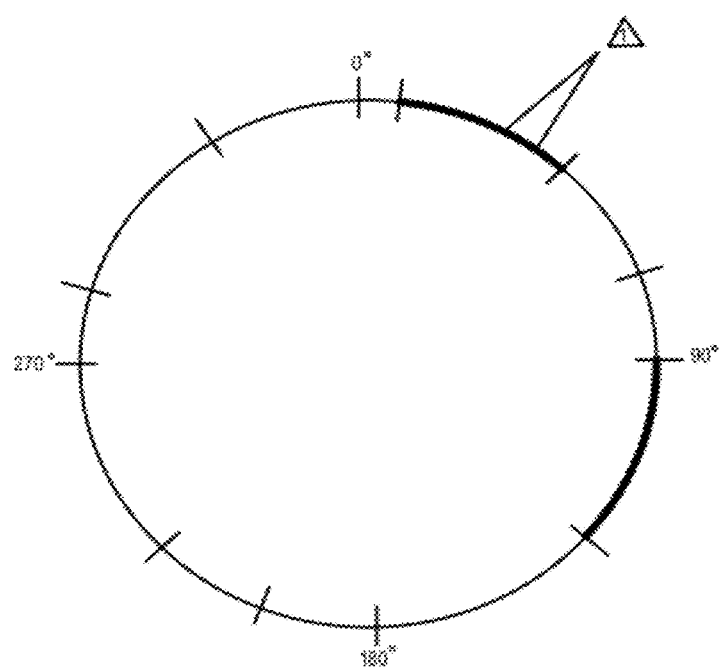
FIG. 5D shows a third display of individual test report critical deviations using the layout of FIG. 5A.

Yet another display embodiment is shown in FIG. 5D. In this case, the presence of the numeral "1" in a triangle indicates that a pathology report has produced a number reporting a test result that is out of a normal range for a tumor marker test result. Specifically, the tumor marker is Ca 27.29. Also reported is the fact that the tumor marker test result was 30 in March of 2007 and 80 in May of 2007. The physician may need to alter therapy or consider a work-up (W/U), such as a biopsy.

Figure 5E:
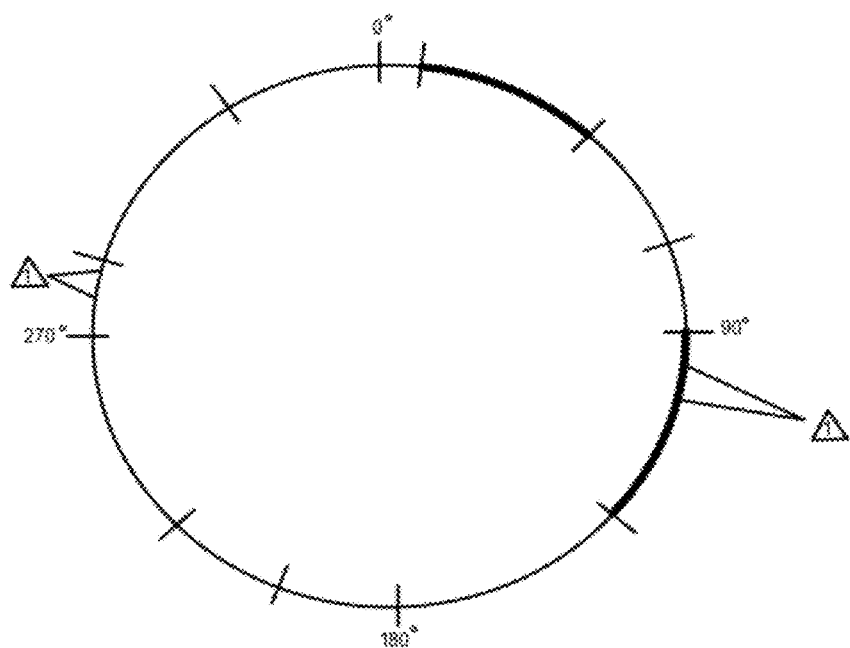
FIG. 5E shows a fourth display of individual test report critical deviations using the layout of FIG. 5A.

Still another display embodiment is shown in FIG. 5E. The circle shown in FIG. 5E shows a "1" in a triangle, indicating that there is a critical result in the medication portion of the circle just below the 90° marker and in the nursing assessment portion of the circle just above the 270° marker. These two indicators are explained in the accompanying note, where the observer is warned that the patient is allergic to penicillin but, for some reason, is being administered doses of penicillin.

Figure 5F:
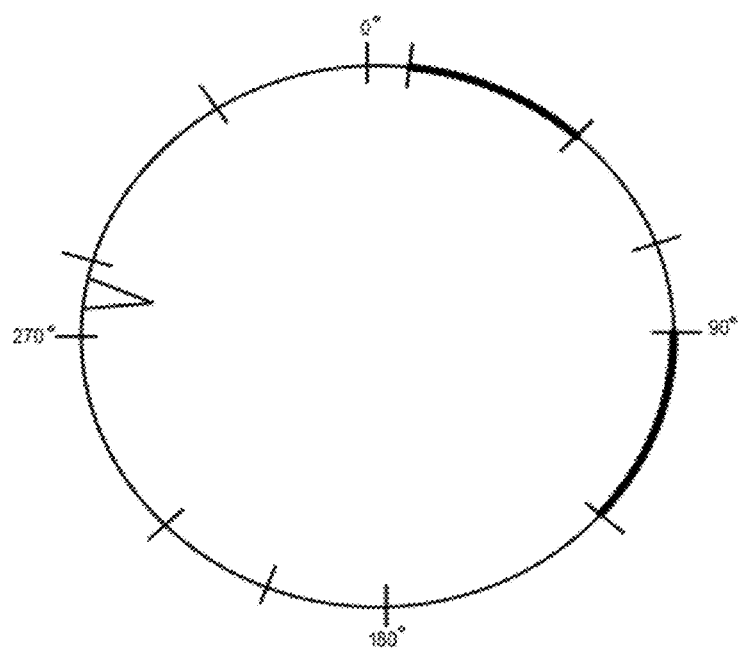
FIG. 5F shows a fifth display of individual test report critical deviations using the layout of FIG. 5A.

FIG. 5F shows a critical result at approximately the 280° position by a small triangular projection jutting into the circle, indicating that the reported data is below the predetermined norm. The nursing assessment is reported in a note under the circle indicating a 6-pound weight loss after the administration of Cisplatin therapy to the patient. Further indication in the note reveals that the patient was subsequently re-hydrated.

Other embodiments of systems and methods of the present invention appear in FIGS. 6A, 6B, 7A, 7B, and 7C. In these embodiments, multiple test results are displayed around a substantially circular shape. Radial lines or rays extending outwardly from the circle indicate a measurement or a test result above a predetermined norm. Radial lines or rays extending inwardly from the circle indicate a measurement of a test result below a predetermined norm. The length of the radial line or ray is a function, for numeric data, of its statistical confidence limits. In these embodiments, data that is one standard deviation norm is rendered as a line of a pre-determined length, data that is two standard deviations away from a norm is shown as a longer line, and so on. Shown below the circular display of data is a box of icons associated with this screen display.

Figure 6A:
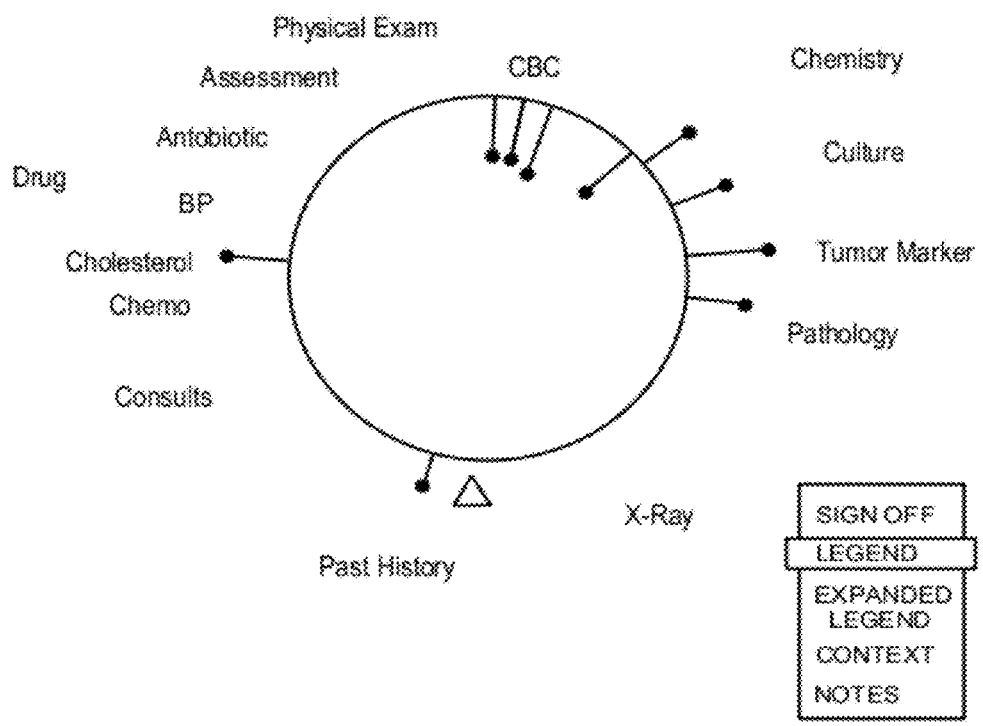
FIG. 6A shows a display layout graphically presenting multiple deviations from a norm along with an explanatory legend identifying the data displayed at a predetermined location on the circular display in an embodiment of the present invention.

In FIG. 6A, the "LEGEND" view has been selected by the user to produce an array of labels identifying the information displayed at various locations around the circle. In FIG. 6A, a circle is displayed along with the appropriate labels to determine the various information displayed at various portions of the circle in this case for an oncologist. One of ordinary skill in the art will understand that physicians practicing in certain specialty areas such as internal medicine, surgery, or urology may desire a custom set of labels pointing them to the information deemed to be most critical to them. In other embodiments, individual physicians may further desire a unique set of labels. In yet other embodiments, an array of general data is used that is useful to physicians irrespective of specialty or useful to nursing staff.

Beginning at the top of the circle shown in FIG. 6A is an indication of CBC. Next is an arcuate sector covering about 45° in which information dealing with Chemistry is reported. The Chemistry sector is followed by several smaller arcuate sectors describing information about Cultures, Tumor Markers, and Pathology. At the bottom of the circle, more subjective information is shown, such as the analysis of x-rays, past history of the patient, and consultation reports from other physicians. In the upper quadrant of the circle on the left side appears information about treatment, including information relating to Chemotherapy, Cholesterol treatment, Blood Pressure, Antibiotics, Assessment, and Physical Exams.

Shown at the bottom of a circle in FIG. 6A is a small triangle. The location and the appearance of this small triangle symbol in the illustrated embodiment is an indication of the need for intervention regarding a particular observation. Thus, a quick scan of the circle by a physician for the appearance of a small triangle quickly alerts the physician that a comparison of a test result or a portion of treatment history has been made and that some intervention may be necessary. The distance of the position of the small triangle from the circle is indicative of the length of time to the next appointment with a physician. In some embodiments, the small triangle is colored with an attention-getting color or flashes.

Figure 6B:
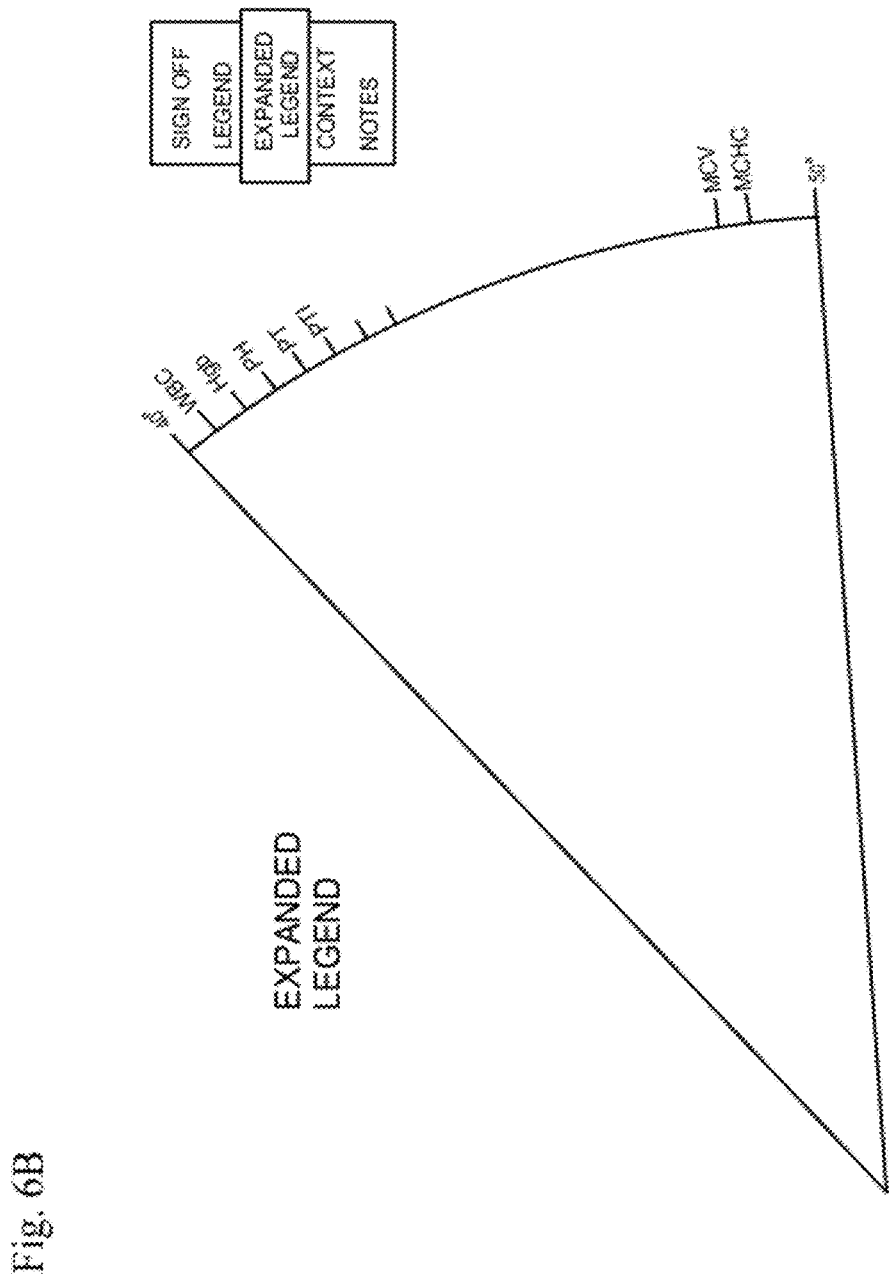
FIG. 6B shows an enlarged sector of the circle shown in FIG. 6A with an expanded legend identifying additional data.

Of particular concern to a physician viewing this display of information shown in FIG. 6A is the Chemistry section. Accordingly, the physician can click on this sector of the circular array of information or highlight this sector and click on an icon, such as a "REVIEW" icon (not shown), to obtain additional details. The additional details in this more granular view are shown in FIG. 6B along with additional labels obtained by using the icon identified as "EXPANDED LEGEND". FIG. 6B shows an enlarged approximately 10° arcuate sector, specifically that arcuate sector which extends from about 40° to about 50° of the circle shown in FIG. 6A. A broader array of test results is shown as radial lines extending outwardly from the arcuate portion of the sector. As with FIG. 6A, a long radial line extending from the arcuate portion of the sector indicates a severely critical result. While not shown in FIG. 6B, some embodiments add further explanatory notes along with the sector shown.

Figure 7A:
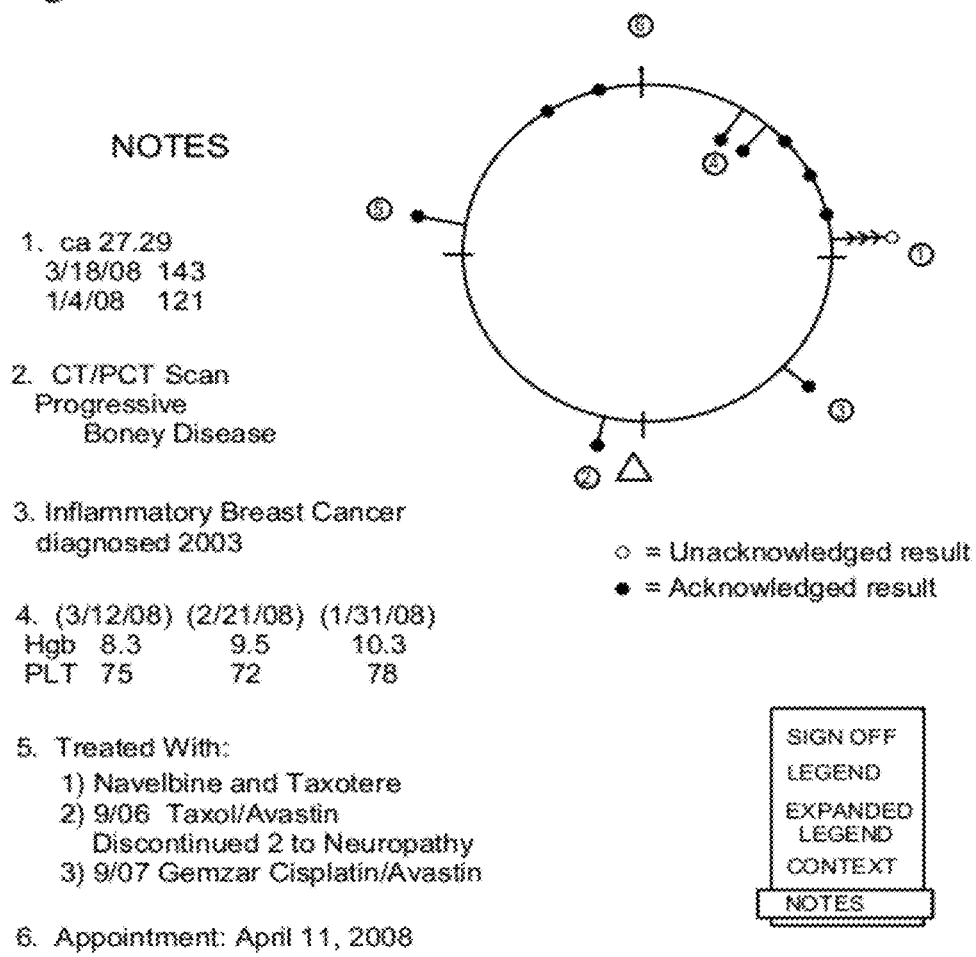
FIG. 7A shows a display layout graphically presenting multiple deviations from a norm along with explanatory notes to assure recognition of the deviations by an attending physician in an embodiment of the present invention.

A physician preferably may display notes under the circle by selecting an icon, such as the "NOTES" icon shown in FIG. 7A. By selecting the "NOTES" icon, the physician sees that the patient has been diagnosed with breast cancer. Hence, the array of information displayed around the circle relates to those categories of information that an oncologist, particularly an oncologist specializing in the treatment of breast cancer, may want to see.

Also shown in FIG. 7A are notes along with a circular array of information. As in the prior embodiments, the notes are keyed to numbers appearing near the radial lines or rays extending outwardly from the circle. Some of the circles at the end of the radial lines are filled in, and some are not. As explained above, a circle which is not filled in indicates that the information has not yet been reviewed by the physician observing the screen shown in FIG. 7A. A filled-in circle shows that the information has been reviewed and acknowledged by the physician. The screen shown in FIG. 7A adds yet another visual indicator not shown in the embodiments described above. This visual indicator is a series of arrows along the radial line or ray at the approximate 90° position near the circle, including the numeral "1" on the right side of the circle. This series of arrows indicates an upward trend in a test result over time. Additional indicators may include different types of highlighting, such as a flashing word or symbol, for different test results or test results above a predetermined level. Such indicators may include colors such as red for severe abnormal indications, amber or yellow for non-severe abnormal indications, and green for abnormal indications that bear watching or have been noted by others as worthy of future attention. Potentially lethal indications may be designated using a special symbol, such as a skull and crossbones symbol.

As in the embodiments shown in FIGS. 5A, 5B, 5C, 5D, 5E and 5F, explanatory notes appear under the circle in FIG. 7A. The multiple notes shown in FIG. 7A correspond to the numbers on the radial lines extending either outwardly from or inwardly into the circle. The explanatory notes provide two functions. First, the order in which the explanatory notes are numbered indicates a suggested priority of the need for multiple responses to intervention-indicated data. For example, the order of the explanatory notes may correspond to the size of the deviation of the data from a norm. As shown in Note 1, the small triangle, explained above as indicating a need for intervention, is further described as showing an appointment with an oncologist on Apr. 11, 2008. Other entries in the Notes indicate the diagnosis of breast cancer in 2003 and the current array of medications being taken by the patient in Note 5. Yet other notes may inform the user that a measurement or test result is so far out of range that it must be a true data anomaly.

The entries in Note 4 relate back to the history of a patient's blood test. Most notable are the changes in hemoglobin (Hgb) and in the platelet count, which contextualizes this important information.

Figure 7B:
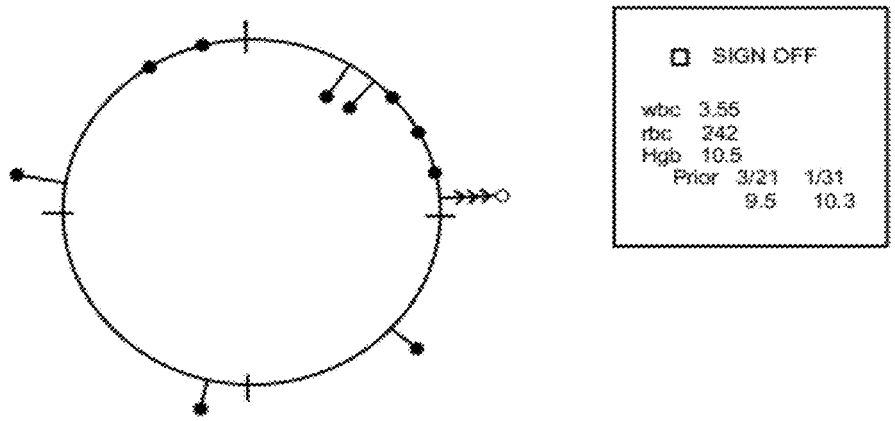
FIG. 7B shows a display layout graphically presenting a sign off screen in an embodiment of the present invention.
Figure 7B:
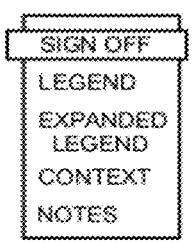

As indicated above, some of the circles which appear in FIG. 7A are open, and some are filled in. When a physician decides to look closer at the information associated with an open circle, such analysis may be accomplished by placing a mouse-movable pointer over the open circle. A display of information as shown in FIG. 7B indicates the review of the information presented in FIG. 7B, and the physician is asked to click on an icon positioned above the more detailed information, such as the one labeled "SIGN-OFF" in FIG. 7B. Clicking on the "SIGN-OFF" icon is an indication that the physician has observed and considered the identified information and causes the open circle appearing in FIG. 7A to be filled in. Information worthy of particular attention may be highlighted by the presence of an arrow. In some embodiments, the user is given the option of going back to the previous screen without signing off, in which case the open circle remains open.

FIG. 7B includes an example of the array of information requiring observation and a recognition of acknowledgement in a "SIGN OFF" box. The information in the sign off box is shown because of its deviation from a norm. Checking the box near the words "SIGN OFF" provides an indication that the physician has observed and acknowledged the data displayed. No further operations with the disclosed system are possible until the "SIGN OFF" box has been checked. As indicated above, once the "SIGN OFF" box has been checked, the open circles in FIG. 7A are filled in.

Figure 7C:
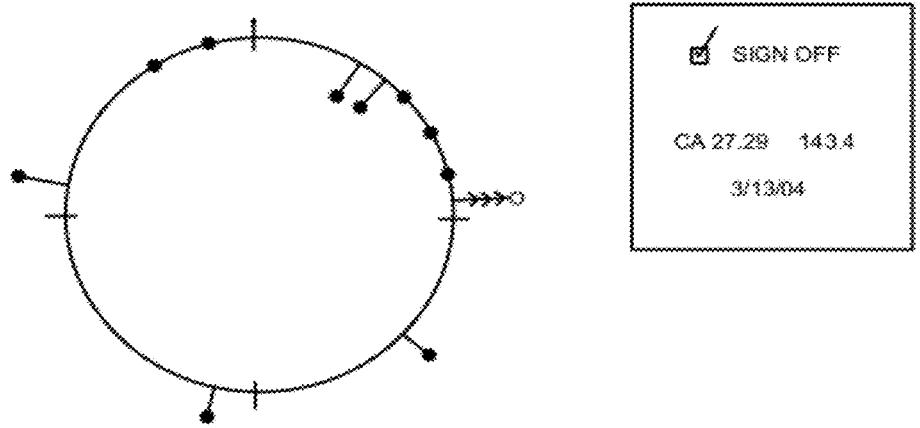
FIG. 7C shows a display layout graphically presenting patient treatment over time in an embodiment of the present invention.

In FIG. 7C another "SIGN OFF" box appears requiring acknowledgement by the user. Once observation of this data has been acknowledged by the user by clicking the box next to the words "SIGN OFF", the user may proceed to a "CONTEXT" display of a more detailed patient history, as shown along the bottom of the screen image.

A still better understanding of the above-described system and method embodiments may be had by a further description of the various icons described above, as follows.

The "LEGEND" icon provides a command to the computer to display identifying information, such as shown in FIG. 5A and in FIG. 6A. Labels of data categories are added to describe the information to be displayed at predetermined locations. For the new user, use of the "LEGEND" icon provides a quick indication of where information of interest appears. Initially, no numbers or test results are shown on the display. A second command or a click on the "LEGEND" icon as shown in FIGS. 5A and 6A causes the labels to disappear as shown in FIG. 7A.

The "EXPANDED LEGEND" icon allows the user to indicate a command to the system to display more detailed information associated with an enlarged display of an arcuate sector. An example of such detailed information appears in FIG. 6B. After the "EXPANDED LEGEND" icon is selected and the micro display of available information is revealed, the user may still click on a designated information identifier to achieve yet more information about a particular measurement.

The "NOTES" icon provides a command which displays the explanatory notes which appear near the macro information display as shown in FIG. 7A, where data is displayed which deviates from a norm or is a data anomaly. Selecting the "NOTES" icon makes the notes appear, and selecting the icon again makes the notes disappear. Each of the numeric identifiers is keyed to written descriptions at the bottom of the screen. As previously indicated, the set of notes is organized so that the highest priority or most deviant or abnormal measurement or test result information preferably appears in the first note. If desired, the displayed notes may be grouped into one or more categories to characterize the criticality of the information displayed.

The specific entries associated with each note include the value of a test result along with any recommended intervention or available historical data putting the test result in a context where it is best understood. As explained below, the information displayed in the notes is the same as the information that may be obtained when an icon identified as "CONTEXT" is selected as shown in FIG. 7C.

If desired, the explanatory notes can be printed out and added to the paper portions of a patient's treatment record. Also if desired, the indication on the screen may be forwarded to another computer at a distant location for consultation with another health care professional. Alternatively, a doctor visiting a hospital away from where his or her patients are located may monitor a patient's condition or the progress of intervention therapy at the doctor's home hospital. In still other situations the information on the screen may be forwarded to a records storage facility or to a provider of medical insurance. While the only limit to the number of notes presented is the size of the screen, a range of 5-10 notes per patient is satisfactory in most instances. If the condition of a patient changes, additional notes may be added, and the numbering of the notes to indicate their priority may be changed.

If a physician wants to look again at a set of test results, the mouse-movable pointer is moved as described above to an area of interest on the macro display of information shown in FIG. 6A to obtain an expanded display as appears in FIG. 6B.

While a routine set of labels for the arcuate sectors of the circle appears as shown in FIG. 5A and in FIG. 6A, "CRITICAL TEST RESULTS" categories may be selected to display only those categories of test results which could have very rapid adverse health consequences for a patient. More particularly, the "CRITICAL TEST RESULTS" categories are established to provide a way for the physician, or his surrogate within a hospital or within a laboratory, to determine what actions need to be taken. Such "CRITICAL TEST RESULTS" categories may be standardized for a specialty practice area or a hospital or according to the preferences of an individual physician. When the "CRITICAL TEST RESULTS" icon is selected, only test results in these categories are displayed as open circles, as shown in FIG. 7A, attached to a radial line. As indicated above, acknowledgement of the observation of a measurement or a test result by the selection of an icon labeled SIGN-OFF icon is needed to fill in each open circle. Those test results which are critical but are readily expressed numerically appear as radial lines extending outwardly from the circular array of information.

As indicated above, a custom set of "CRITICAL TEST RESULTS" may be selected by the user. Further, the user may determine at what level a measurement or a test result is determined to be abnormal or an anomaly. This customizing feature can be adopted to multiple types of practices and even to the preferences of individual practitioners. Selecting a customized set of "CRITICAL TEST RESULTS" displays those test results best displayed as a numerical value. When selected, the information shown includes deviations from the 95% confidence limits of either the population at large or whatever confidence level is selected with respect to a data set. Values above the confidence limits appear as radial lines extending outwardly from the circle and values below the confidence litmus appear as radial lines extending into the space within the circle. Once again, the open circle and filled circle system described above is exemplary of a method used to determine if certain items of data have been observed. Further, and as indicated above, the radial line extending to the circle may include arrow markings indicating a decreasing trend, an increasing trend, or stability.

As shown in FIG. 7C, a "CONTEXT" icon may be available to enable a physician to obtain a history of measurements or a chronology of test results. Further information made available may be a history of the test type and previous interventions made. Such interventions may include medications administered orally or by IV.

Those of ordinary skill in the art will understand that displays of information as shown in FIG. 7A may be laid one over another to note changes in the test results of a particular patient or the characteristics of a patient population. When displays of information from multiple patients are stacked up, specific trends, such as high levels of a particular substance in patients such as a pollutant found in a selected geographic area or the effectiveness of a particular health care facility in treating a medical condition, may be identified. Such displays of aggregated information from multiple patients preferably enable physicians or bio-statisticians to identify situations where significant data resides (i.e., at the tail of a normal data distribution). This data collection can then be further analyzed.

A further utility preferably provided by the system and method is the assembly of predetermined sub-sets or strings of data such as shown in FIG. 6B. Such sub-sets or strings of data may be displayed on a two-dimensional array or on a rotatable two-dimensional representation of a three-dimensional object as found in CAD drawings. The use of such utility may be particularly helpful in data mining or forensic analysis, where seemingly unrelated sets of data are compared to determine previously unfound similarities or relationships among certain conditions reported by measurements or test results.

By aggregating sets of data constructed as described in the preceding paragraph, such as stacking multiple images one-over-the-other, certain characteristics of a data universe may be determined. Such critical data appears in the "tails" of a normal distribution and may signal a heretofore unrecognized phenomenon.

Other Applications

Those of ordinary skill in the art will understand that the above embodiments in a health care context are illustrative and that the system and method may be used in any situation where information is presented to a professional for the exercise of professional judgment regarding any actions or interventions to be taken or not taken.

Other fields in which systems and methods of the present invention may be used include, but are not limited to, transportation, military, financial, and business management.

In the field of transportation, systems and methods may be applied to airplane flight control and Transportation Security Administration (TSA) passenger screening.

In the military, systems and methods may be used to manage troops and supplies and determine deployment readiness.

In the financial field, systems and methods may be used to compile credit reports and track financial trends for an individual or a company.

In the field of business management, systems and methods may be used to track production and inventory and to evaluate personnel and work flow.

By use of the system and method, users are preferably able to rapidly and consistently identify changes in data representing a particular measurement or test result. Once identified, the changes in the measurement or test result are supported by access to a prioritized subset of vital information, providing both additional information and recommended courses of action to enable the implementation of an intervention, if such intervention is needed. Continuous updating of the information display allows a user to identify and assess the seriousness of a change in reported information. Accordingly, errors from missing important data or acting improperly with respect to deviations in reported data from a predetermined norm or a data anomaly become substantially reduced.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of aggregating, categorizing, and ordering a set of data of any size comprising a plurality of reports, each report comprising at least one data value, the method comprising the steps of:
 a) a computer categorizing each report into one of a plurality of data types;
 b) the computer comparing the at least one data value in each report to at least one test criterion for the data value and categorizing the report as a non-critical report including only non-critical data values or a critically abnormal report including at least one critically abnormal data value; and
 c) the computer electronically displaying a base predetermined array in a first part of an electronic display screen as a plurality of buttons, each button representing the non-critical reports of one of the plurality of data types or the critically abnormal reports of one of the plurality of data types at a predetermined display location in the base predetermined array, each button linking directly to a stack of either a set of aggregated data of the non-critical reports or a set of aggregated data of the critically abnormal reports of one of the plurality of data types, wherein upon application of the button by a user, the report on top of the stack associated with the button is displayed in a second part of the electronic display screen.

2. The method of claim 1, wherein the base predetermined array is based on a circular geometric structure to allow an optimal interface with a circular visual field of a human retina.

3. The method of claim 1, wherein the base predetermined array is based on a geometric structure selected from the group consisting of a straight line, a curved line, a triangle, a rectangle, an oval, a sphere, a cone, a pyramid, and a cube.

4. The method of claim 1, wherein the computer displays each report, based on a button application by the user, in the second part of the electronic display screen such that the base predetermined array remains displayed in the first part of the electronic display screen.

5. The method of claim 1 further comprising the step of the computer receiving an input of a modification of at least one of the at least one test criterion by the user.

6. The method of claim 5 further comprising the step of the computer re-comparing relevant data values to the test criterion based on the modification to re-categorize the reports as non-critical reports or critically abnormal reports after the user modifies the test criterion.

7. The method of claim 1, wherein each button is displayed as a numeral inside a circle, the numeral representing a number of unreviewed data values linked to the button.

8. The method of claim 1, wherein the data are medical data.

9. The method of claim 8 further comprising the step of the computer displaying a link to a patient predetermined array, wherein the patient predetermined array is linked to all medical data associated with a patient for the patient associated with the report being displayed on the second part of the electronic display screen.

10. The method of claim 9 further comprising the computer displaying the patient predetermined array in place of the base predetermined array when the user selects the link to the patient predetermined array.

11. The method of claim 8, wherein the buttons are linked to all of the test results for which the user is responsible to review but has not yet indicated as reviewed.

12. The method of claim 8 further comprising the steps of:
the computer receiving a new report, wherein the new report includes at least one critically abnormal data value;
the computer categorizing the new report into one of the plurality of data types;
the computer categorizing the new report as a new critically abnormal report; and
the computer sending an electronic message to a user responsible for reviewing the new report, thereby alerting the user of the new critically abnormal report.

13. The method of claim 1 further comprising:
the computer filtering the set of data using at least one filter criterion to obtain at least one filtered data set; and
the computer electronically displaying a filtered predetermined array based on the filtered data set in place of the base predetermined array.

14. The method of claim 13 further comprising the computer displaying a filter link with the base predetermined array and a base link with the filtered predetermined array such that the user can toggle between the base predetermined array and the filtered predetermined array by selecting the filter link and the base link with a single selection.

15. The method of claim 1, wherein the test criterion comprises comparing a second data value for a test result type associated with a patient at a second time to a first data value for the test result type associated with the patient at a first time prior to the second time to determine whether a change between the first data value and the second data value falls within a predetermined threshold making the second data value a non-critical data value or outside the predetermined threshold making the second data value a critically abnormal data value.

16. The method of
claim 1, wherein selection of a portion of the predetermined array by a user displays subsidiary data associated with the portion of the predetermined array with at least a 360-fold enrichment of detail in the portion of the predetermined array.

17. The method of claim 16, wherein selection of a sub-portion of the portion of the predetermined array by a user displays sub-subsidiary data associated with the sub-portion of the predetermined array with at least a 360-fold enrichment of detail in the sub-portion of the predetermined array.

18. A method of reviewing a set of data of any size comprising a plurality of reports, each report comprising at least one data value, the method comprising the steps of:
a) visually scanning a first part of an electronic screen displaying a plurality of buttons in a base predetermined array, each button being at a predetermined display location in the base predetermined array, each button representing a stack of a set of aggregated data of the set of data of either at least one non-critical report or at least one critically abnormal report of one of a plurality of data types, the plurality of reports having been categorized into the plurality of data types and into the non-critical reports and the critically abnormal reports;
b) selecting a first button of the plurality of buttons representing a first stack of a first set of aggregated data of at least one critically abnormal report of one of the plurality of data types to cause the critically abnormal report on top of the stack of the data type associated with the button to be displayed on a second part of the electronic screen, wherein the critically abnormal reports are sequentially viewable from a top of the stack down; and
c) evaluating the critically abnormal report.

* * * * *